(12) United States Patent
Hill et al.

(10) Patent No.: US 9,890,190 B2
(45) Date of Patent: Feb. 13, 2018

(54) PREPARATION OF LONG SYNTHETIC OLIGONUCLEOTIDES BY SQUARATE CONJUGATION CHEMISTRY

(71) Applicant: Agilent Technologies, Inc., Santa Clara, CA (US)

(72) Inventors: Kenneth W. Hill, Lyons, CO (US); Douglas J. Dellinger, Boulder, CO (US); Benjamin D. Lunstad, Erie, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/051,511

(22) Filed: Feb. 23, 2016

(65) Prior Publication Data

US 2016/0244820 A1    Aug. 25, 2016

Related U.S. Application Data

(60) Provisional application No. 62/120,298, filed on Feb. 24, 2015.

(51) Int. Cl.
  *C07H 21/02* (2006.01)
  *C07H 21/04* (2006.01)
  (Continued)

(52) U.S. Cl.
  CPC .............. *C07H 21/04* (2013.01); *C07H 1/00* (2013.01); *C12Q 1/6806* (2013.01); *C12Q 1/6837* (2013.01)

(58) Field of Classification Search
  CPC ..................................................... C07H 21/04
  (Continued)

(56) References Cited

U.S. PATENT DOCUMENTS 5,714,320 A    2/1998    Kool
6,140,494 A    10/2000   Hamilton et al.
(Continued)

FOREIGN PATENT DOCUMENTS

CN    102459301 A    5/2015
JP    2005247706    9/2005
(Continued)

OTHER PUBLICATIONS

Sato (JACS 2002, 124, pp. 12715-12724).*
(Continued)

*Primary Examiner* — Jezia Riley

(57) ABSTRACT

Methods of conjugating oligonucleotides are provided. The methods may include: activating a terminal of first oligonucleotide using a squarate reagent to produce an activated first oligonucleotide; and binding the first oligonucleotide and a second oligonucleotide to a splint oligonucleotide; to conjugate the activated first oligonucleotide with a terminal of the second oligonucleotide via a squaramide linkage to produce a squaramide-linked oligonucleotide. Also provided are oligonucleotides that include a squaramide internucleoside linkage. Compositions are provided that include a first oligonucleotide including 300 or more nucleosides and at least one squaramide internucleoside linkage; and a second complementary oligonucleotide not including a squaramide linkage. Kits and compositions for practicing the subject methods are also provided.

19 Claims, 13 Drawing Sheets

(51) Int. Cl.
*C12Q 1/68* (2006.01)
*C07H 1/00* (2006.01)

(58) Field of Classification Search
USPC .................................................. 536/23.1, 25.3
See application file for complete search history.

(56) References Cited

U.S. PATENT DOCUMENTS

| | | | |
|---|---|---|---|
| 2011/0092806 A1 | 4/2011 | Port et al. | |
| 2012/0302453 A1 | 11/2012 | Lugade et al. | |
| 2014/0194324 A1* | 7/2014 | Gormley | C12Q 1/6834 506/17 |

FOREIGN PATENT DOCUMENTS

| | | |
|---|---|---|
| WO | WO 98/30575 | 7/1998 |
| WO | WO2009156421 | 12/2009 |
| WO | WO 2013176844 | 11/2013 |
| WO | WO 2013176845 | 11/2013 |

OTHER PUBLICATIONS

El-Sagheer, et al., "Synthesis and Polymerase Chain Reaction Amplification of DNA Strands Containing an Unnatural Triazole Linkage", J. Am. Chem. Soc., 2009, 131: 3958-3964.

Didenko, et al. "Technical Advance—Biotin-Labeled Hairpin Oligonucleotides Probes to Detect Double-Strand Breaks in DNA in Apoptotic Cells" American Journal of Pathology, 1998, 152(4): 897-902.

Drosdziok, et al. "H-labelled alkyl-nucleotides, -nucleosides and -bases for the immunoanalytical quantification of DNA damage and repair" Journal of Labelled Compounds and Radiopharmaceuticals, 2003, 46(9): 815-835.

El-Sagheer, et al. "Click Nucleic Acid Ligation: Applications in Biology and Nanotechnology" Accounts of Chemical Research 2012, 45(8): 1258-1267.

Onaran, et al. "Squaric Acid-Based Peptidic Inhibitors of Matrix Metalloprotease-1 (MMP-1)" J. Org. Chem. 2005, 70 (26): 10792-10802.

Sato, et al. "Synthesis and Properties of a New Oligonucleotide Analogue Containing an Internucleotide Squaryl Amide Linkage" Nucleic Acids Research Supplement No. 1, 2001, 121-122.

Sato, et al. "Synthesis and Structural Properties of New Oligodeoxynucleotide Analogues Containing a 2',5'-Internucleotidic Squaryldiamide Linkage Capable of Formation of a Watson-Crick Base Pair with Adenine and a Wobble Base Pair with Guanine at the 3'-Downstream Junction Site" Eur. J. Org. Chem. 2004, 2142-2150.

Stark, et al. "An RNA Ligase-Mediated Method for the Efficient Creation of Large, Synthetic RNAs" RNA, 2006, 12: 2014-2019.

Veronese, et al. "PEGylation, successful approach to drug delivery" Drug Discovery Today, 2005, 10(21): 1451-1458.

Wurm, et al. "Squaric acid mediated synthesis and biological activity of a library of linear and hyperbranched poly (glycerol)-protein conjugates", Biomacromolecules, 2012, 13(4): 1161-71.

Yan, et al. "Preparation of Carbohydrate-Oligonucleotide Conjugates Using the Squarate Spacer" Bioorganic and Medicinal Chemistry Letters, 2007, 17: 6535-6538.

Zhao, et al. "Preparation of mannosylated oligoribonucleotides", Nucleic Acids Symp Ser (Oxf), 2008, (52): 89-90.

Zhao, et al. "Synthesis and characterization of mannosylated oligoribonucleotides", Carbohydr Res. 2009, 344(16): 2137-43.

* cited by examiner

FIG. 4
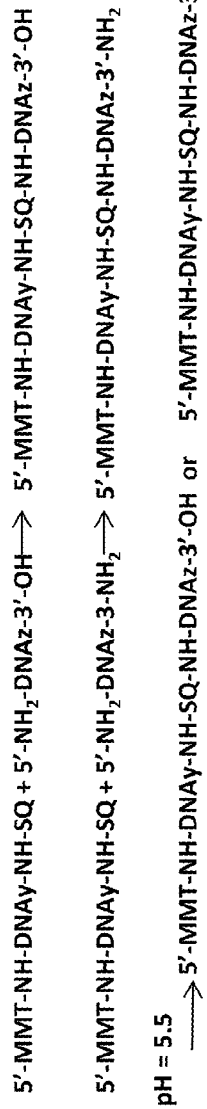
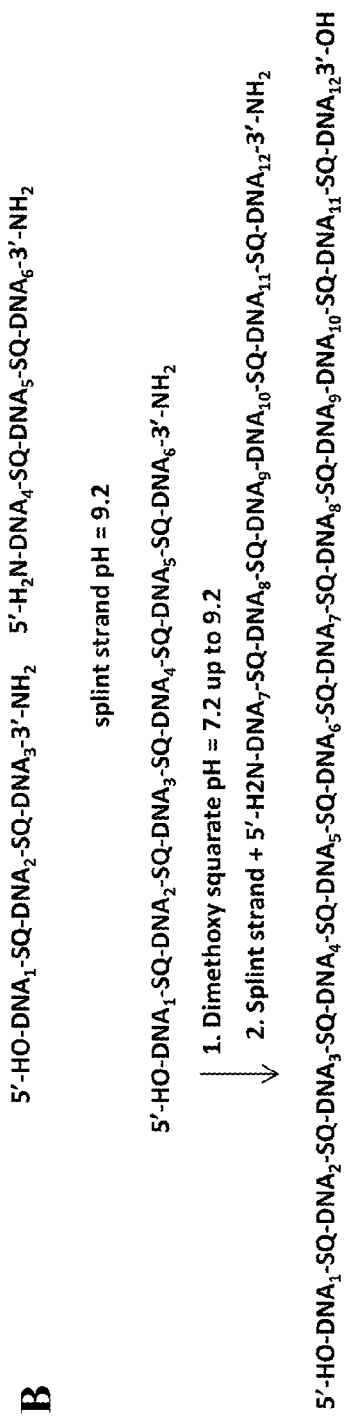

SEQUENCE LISTING

<160> NUMBER OF SEQ ID NOS: 18

<210> SEQ ID NO 1
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)...(26)
<223> OTHER INFORMATION: squaramide linkage

<400> SEQUENCE: 1
atatagatgc cgtcctagcg ctcgttccag cgatgccagt tgggcacagg aaagatactt    60

<210> SEQ ID NO 2
<211> LENGTH: 31
<212> TYPE: DNA
<213> ORGANISM: Artificial Sequence

```
<220> FEATURE:
<223> OTHER INFORMATION: Synthetic oligonucleotide

<400> SEQUENCE: 2
ctggcatcgc tggaacgagc gctactagga c                              31

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
catcgctgga acgagcgcta                                           20

<210> SEQ ID NO 4
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 4
caucgcugga acgagcgcua                                           20

<210> SEQ ID NO 5
<211> LENGTH: 55
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1
<223> OTHER INFORMATION: 5'-NH2 terminal

<400> SEQUENCE: 5
tccacgatgc cagcggttgg ttgcgctggc atcgctggaa cgagcggcgc tagga    55

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 25
<223> OTHER INFORMATION: 3'-NH-squarate terminal

<400> SEQUENCE: 6
atatagatgc cgtcctagcg ctcgt                                     25

<210> SEQ ID NO 7
<211> LENGTH: 79
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)...(26)
<223> OTHER INFORMATION: squaramide linkage

<400> SEQUENCE: 7
atatagatgc cgtcctagcg ctcgttccag cgatgccagc ggttggttgc gctggcatcg   60
```
ctggaacgag cgctaggac                                              79

<210> SEQ ID NO 8
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)...(8)
<223> OTHER INFORMATION: squaramide linkage

<400> SEQUENCE: 8
cgctcgttcc agcg                                                   14

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 34
<223> OTHER INFORMATION: 3'-NH2 terminal

<400> SEQUENCE: 9
gcagauguag uguuucaaca guuuuagagc uact                             34

<210> SEQ ID NO 10
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 34
<223> OTHER INFORMATION: 3'NH-squarate terminal

<400> SEQUENCE: 10
gcagauguag uguuucaaca guuuuagagc uact                             34

<210> SEQ ID NO 11
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1
<223> OTHER INFORMATION: 5'-amino terminal

<400> SEQUENCE: 11
tguagcaagu uaaaauaagg cuaguccguu aucaacuuga aaaguggca ccgagucggu  60 gcuuuu                                                            66

<210> SEQ ID NO 12
<211> LENGTH: 100
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)...(35)
<223> OTHER INFORMATION: squaramide linkage

<400> SEQUENCE: 12
gcagauguag uguuucaaca guuuuagagc uacuugaugc aaguuaaaau aaggcuaguc     60
cguuaucaac uugaaaaagu ggcaccgagu cggugcuuuu                          100

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 27
<223> OTHER INFORMATION: 3'-amino terminal

<400> SEQUENCE: 13
gcagauguag uguuucaaca guuuuat                                        27

<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 27
<223> OTHER INFORMATION: 3'-NH-squarate terminal

<400> SEQUENCE: 14
gcagauguag uguuucaaca guuuuat                                        27

<210> SEQ ID NO 15
<211> LENGTH: 73
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1
<223> OTHER INFORMATION: 5'-NH2 terminal

<400> SEQUENCE: 15
tgcuagaaau agcaaguuaa aauaaggcua guccguuauc aacuugaaaa aguggcaccg     60
agucggugcu uuu                                                       73

<210> SEQ ID NO 16
<211> LENGTH: 100
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (27)...(28)
<223> OTHER INFORMATION: squaramide linkage

<400> SEQUENCE: 16
gcagauguag uguuucaaca guuuuattgc uagaaauagc aaguuaaaau aaggcuaguc     60
cguuaucaac uugaaaaagu ggcaccgagu cggugcuuuu                          100

```
<210> SEQ ID NO 17
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1
<223> OTHER INFORMATION: 5'-NH2-(CH2)6 linker teminal

<400> SEQUENCE: 17
tguagcaagu uaaaauaagg cuaguccguu aucaacuuga aaaguggca ccgagucggu      60 gcuuuu                                                                66

<210> SEQ ID NO 18
<211> LENGTH: 100
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (34)...(35)
<223> OTHER INFORMATION: squaramide linkage

<400> SEQUENCE: 18
gcagauguag uguuucaaca guuuuagagc uacttguagc aaguuaaaau aaggcuaguc      60
cguuaucaac uugaaaaagu ggcaccgagu cggugcuuuu                           100
```

PREPARATION OF LONG SYNTHETIC OLIGONUCLEOTIDES BY SQUARATE CONJUGATION CHEMISTRY

CROSS-REFERENCE TO RELATED APPLICATIONS

Pursuant to 35 U.S.C. § 119(e), this application claims priority to the filing date of the U.S. Provisional Application No. 62/120,298, filed on Feb. 24, 2015, the disclosure of which application is herein incorporated by reference in its entirety.

INTRODUCTION

Preparing long oligonucleotides by the standard phosphoramidite solid phase synthesis method is exponentially dependent on the coupling efficiencies of each nucleotide addition. Lengths of 100 bases are not uncommon from syntheses done at 1-10 µmole scale. Purification of the Full Length Product (FLP) from the truncated species of similar size becomes increasingly difficult as the length grows. The practical length that can be synthesized and purified varies from approximately 70 bases at mmole scales, approximately 100-150 mers at 1 umole scale and possibly doubling or more when synthesized on DNA/RNA microarrays. Longer oligonucleotides may be made by enzymatic ligations of smaller strands to each other.

SUMMARY

Methods of conjugating oligonucleotides are provided. The methods may include: activating a terminal of first oligonucleotide using a squarate reagent to produce an activated first oligonucleotide; and binding the first oligonucleotide and a second oligonucleotide to a splint oligonucleotide; to conjugate the activated first oligonucleotide with a terminal of the second oligonucleotide via a squaramide linkage to produce a squaramide-linked oligonucleotide. Also provided are oligonucleotides that include a squaramide internucleoside linkage. Compositions are also provided that include a first oligonucleotide including 300 or more nucleosides and at least one squaramide internucleoside linkage; and a second complementary oligonucleotide not including a squaramide linkage. Kits and compositions for practicing the subject methods are also provided.

BRIEF DESCRIPTION OF THE FIGURES

The skilled artisan will understand that the drawings, described below, are for illustration purposes only. The drawings are not intended to limit the scope of the present teachings in any way.

FIG. 4 panels A and B, shows exemplary squarate based convergent block coupling of basic subunits (5'OH-DNAx-$NH_2$-3', 5'-MMT-NH-DNAy-NH-SQ-3',5'-$NH_2$-DNAz-3'$NH_2$ and 5'-$NH_2$-DNAz-3'OH) to produce a long oligonucleotide (SQ=squarate linkage): (Panel A) Block Synthesis where use of MMT protection allowing the synthesis of the middle and 3' end blocks; (Panel B) Multi-block assembly using squarate linkages.

DEFINITIONS

Figure 1:
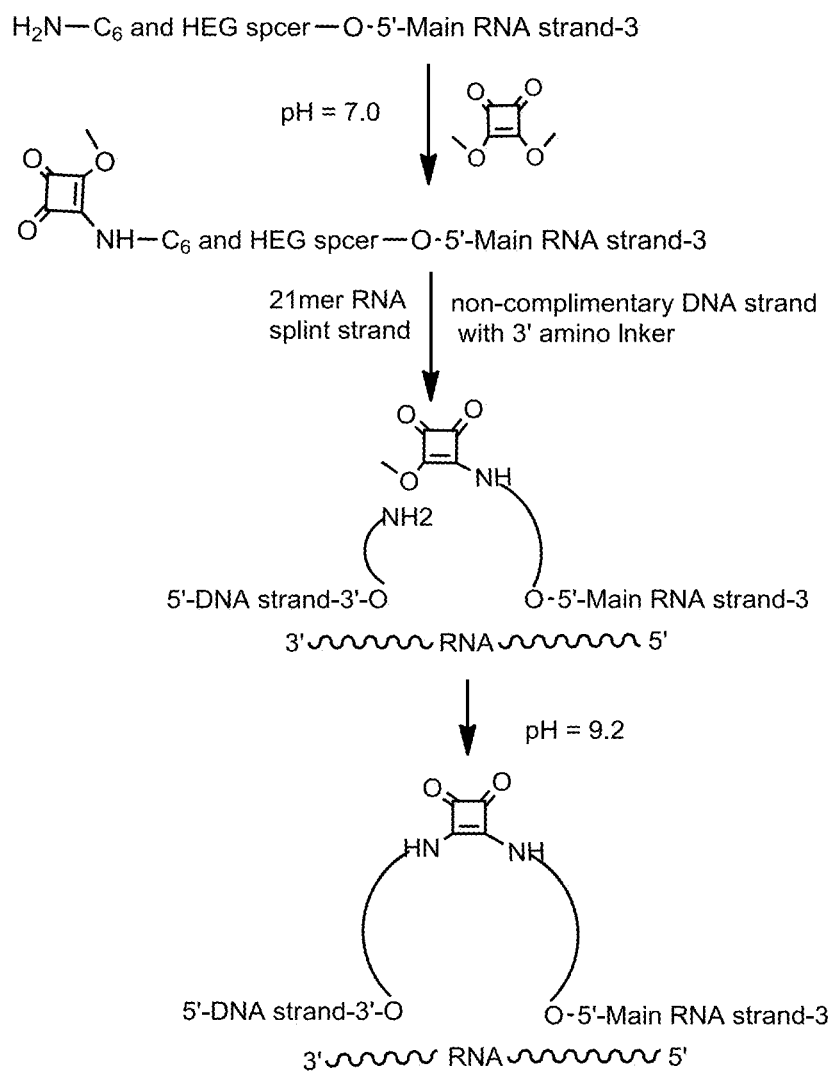
FIG. 1 schematically illustrates squarate mediated conjugation of two non-complimentary DNA with RNA using an RNA splint.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan- 1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Acyl" by itself or as part of another substituent refers to a radical —C(O)R$^{30}$, where R$^{3o}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is (C$_7$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). In certain embodiments, an arylalkyl group is (C$_7$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —$O^-$, =O, —$OR^{60}$, —$SR^{60}$, —$S^-$, =S, —$NR^{60}R^{61}$, =$NR^{60}$, $CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, $OS(O)_R^{60}$, —$P(O)(O^{31})_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"Primary amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Halo" or "halogen" refers to fluoro, chloro, bromo, and iodo. The term "hydroxyamino" refers to the group —NHOH. "Nitro" refers to the group —$NO_2$. "Oxo" refers to the atom (=O).

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cylcoalkyl, $SO_2$-cycloalkenyl, $SO_2$-substituted cylcoalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

"Sulfonyloxy" refers to the group —$OSO_2$-alkyl, $OSO_2$-substituted alkyl, $OSO_2$-alkenyl, $OSO_2$-substituted alkenyl, $OSO_2$-cycloalkyl, $OSO_2$-substituted cylcoalkyl, $OSO_2$-cycloalkenyl, $OSO_2$-substituted cylcoalkenyl, $OSO_2$-aryl, $OSO_2$-substituted aryl, $OSO_2$-heteroaryl, $OSO_2$-substituted heteroaryl, $OSO_2$-heterocyclic, and $OSO_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein. "Thiol" refers to the group —SH. "Thioxo" or the term "thioketo" refers to the atom (═S).

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

Numeric ranges are inclusive of the numbers defining the range.

As used herein, the terms "nucleoside" and "nucleoside moiety" reference a nucleic acid subunit including a sugar group and a heterocyclic base, as well as analogs of such sub-units, such as a modified or naturally occurring deoxyribonucleoside or ribonucleoside or any chemical modifications thereof. Other groups (e.g., protecting groups) can be attached to any component(s) of a nucleoside. Modifications of the nucleosides include, but are not limited to, 2'-, 3'- and 5'-position sugar modifications, 5- and 6-position pyrimidine modifications, 2-, 6- and 8-position purine modifications, modifications at exocyclic amines, substitution of 5-bromo-uracil, and the like. Nucleosides can be suitably protected and derivatized to enable oligonucleotide synthesis by methods known in the field, such as solid phase automated synthesis using nucleoside phosphoramidite monomers, H-phosphonate coupling or phosphate triester coupling.

A "nucleotide" or "nucleotide moiety" refers to a sub-unit of a nucleic acid which includes a phosphate group, a sugar group and a heterocyclic base, as well as analogs of such sub-units. Other groups (e.g., protecting groups) can be attached to any component(s) of a nucleotide. The term "nucleotide", may refer to a modified or naturally occurring deoxyribonucleotide or ribonucleotide. Nucleotides in some cases include purines and pyrimidines, which include thymidine, cytidine, guanosine, adenine and uridine.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, dimethylacetamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars and conventional stereoisomers, but other sugars as well, including L enantiomers and alpha anomers. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features such that they can be considered mimetics, derivatives, having analogous structures, or the like, and include, for example, polynucleotides or oligonucleotides incorporating non-natural (not usually occurring in nature) nucleotides, unnatural nucleotide mimetics such as 2'-modified nucleosides including but not limited to 2'-fluoro, 2'-O-alkyl, O-alkylamino, O alkylalkoxy, protected O-alkylamino, O-alkylaminoalkyl, O-alkyl imidazole, and polyethers of the formula (O-alkyl)m such as linear and cyclic polyethylene glycols (PEGs), and (PEG)-containing groups, locked nucleic acids (LNA), peptide nucleic acids (PNA), oligomeric nucleoside phosphonates, and any polynucleotide that has added substituent groups, such as protecting groups or linking groups.

As used herein, the terms "internucleotide linkage", "internucleotide bond" and "nucleotide bond" are used interchangeably and refer to a chemical linkage between two nucleoside moieties, such as the squaramide linkage (e.g., as described herein) or the phosphodiester linkage in nucleic acids found in nature, or their thiolated or dithiolated equivalents or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group. An internucleotide bond may include a squaramide linkage.

The term "oligonucleotide", as used herein, refers to a polynucleotide formed from a plurality of linked nucleotide units as defined above. The nucleotide units each include a nucleoside unit linked together via a phosphate linking group, or an analog thereof. The term oligonucleotide also refers to a plurality of nucleotides that are linked together via linkages other than phosphate linkages such as phosphorothioate linkages or squaramide linkages. The oligonucleotide may be naturally occurring or non-naturally occurring. In some cases, the oligonucleotides may include ribonucleotide monomers (i.e., may be oligoribonucleotides) and/or deoxyribonucleotide monomers.

The term "DNA", or "deoxyribonucleic acid", as used herein, refers to a polynucleotide or oligonucleotide that comprises at least one deoxyribonucleotide residue. The term "RNA", or "ribonucleic acid", as used herein, refers to a polynucleotide or oligonucleotide that comprises at least one ribonucleotide residue.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present invention is stable, e.g. to physiological conditions, until it is contacted with a cleavage-inducing stimulus, e.g., an agent such as an enzyme or other cleavage-inducing agent such as chemical agent or light. Exemplary conditions are set forth below.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, methods for of conjugating oligonucleotides are described first in greater detail. Next, oligonucleotides and compositions of interest for practicing the subject methods are reviewed. Kits are also described.

Methods for Conjugating Oligonucleotides

As summarized above, aspects of the invention include methods of conjugating oligonucleotides. In some embodiments, the method includes activating a terminal of first oligonucleotide using a squarate reagent to produce an activated first oligonucleotide; and binding the first oligonucleotide and a second oligonucleotide to a splint oligonucleotide; to conjugate the activated first oligonucleotide with a terminal of the second oligonucleotide via a squaramide linkage to produce a squaramide-linked oligonucleotide.

Squarate Reagent

Figure 2:
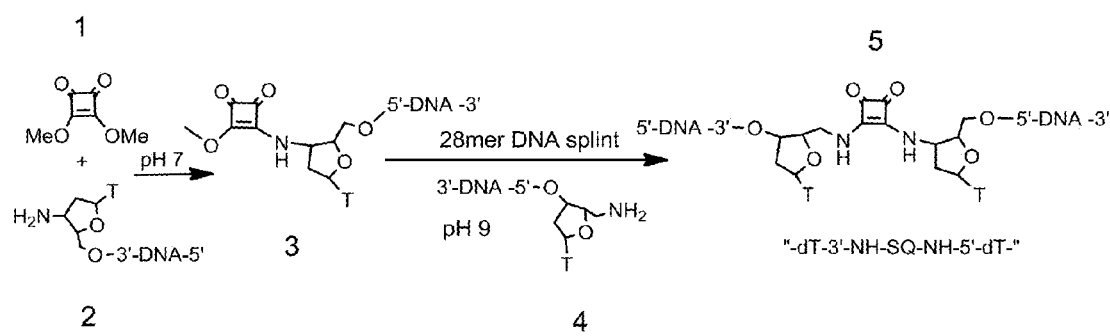
FIG. 2 illustrates a scheme for coupling of two strands of amine modified DNA (2 and 4) using a squarate reagent (1) to produce a squaramide-linked oligonucleotide (5) via a monosquaramide activated oligonucleotide (3).

Aspects of the method include activating a terminal of an oligonucleotide using a squarate reagent. By "activating a terminal" is meant that the terminal of the first oligonucleotide is chemically modified to include a terminal functional group (e.g., a monosquaramide group) that is capable of a further coupling reaction to produce a squaramide linkage. As such, the oligonucleotide may be referred to as "an activated oligonucleotide." FIG. 2 illustrates the activating of a terminal group (e.g., a 3'-amino) by reaction with a squarate reagent (1) to produce an activated oligonucleotide including a terminal monosquaramide group (3). Any convenient squarate reagents may be utilized in the subject methods. As used herein, the term "squarate reagent" refers to a chemical reagent that includes a cyclobutenedione core structure that is capable of forming covalent bonds to the 3 and/or 4 positions of the cyclobutenedione, such that the reagent is capable of coupling with a terminal functional group of an oligonucleotide (e.g., a terminal-modified oligonucleotide).

In some embodiments, the squarate reagent is described by formula (I):

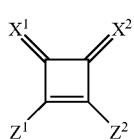

(I)

wherein $X^1$ and $X^2$ are each independently O or S; and $Z^1$ and $Z^2$ are each independently a leaving group.

In certain embodiments of formula (I), $X^1$ is O and $X^2$ is S. In certain embodiments of formula (I), $X^1$ is S and $X^2$ is O. In certain embodiments of formula (I), $X^1$ and $X^2$ are both S. In certain embodiments of formula (I), $X^1$ and $X^2$ are both O. In some instances of formula (I), $X^1$ and $X^2$ are both O, but one or both of the downstream groups corresponding to $X^1$ and $X^2$ are thionated during a subsequent downstream step of the subject methods.

Any convenient leaving groups may be utilized in the squarate reagent. In some embodiments, the squarate reagent includes alkoxy leaving groups. Leaving groups of interest include, but are not limited to, halogens (e.g., chloro, bromo or iodo), alkoxy, substituted alkoxy, aryloxy, substituted aryloxy, heteroaryloxy, substituted heteroaryloxy, acyloxy, substituted acyloxy, alkylsulfonate (e.g., mesylate), substituted alkylsulfonate, arylsulfonate (e.g., mesylate), substituted arylsulfonate (tosyl), diazo, and the like. In certain instances, the cyclobutenedione core is thiolated, e.g., monothionated or dithionated. Squarate reagents of interest include, but are not limited to: diethyl squarate, dimethyl squarate and diisopropyl squarate.

Any convenient methods and squarate moieties or reagents may be adapted for use in the subject methods in order to activate a terminal of an oligonucleotide using a squarate reagent. Methods and reagents of interest include, but are not limited to, those methods and materials described by Onaran et al. "Squaric Acid-Based Peptidic Inhibitors of Matrix Metalloprotease-1 (MMP-1)" J. Org. Chem. 2005 Dec. 23; 70(26); and by Hill et al. in WO2013/176844, the disclosure of which is incorporated herein by reference in its entirety.

A Terminal of a First Oligonucleotide

A variety of terminal functional groups may be incorporated into the first and/or second oligonucleotides that are to be coupled using the subject methods. In some instances, the terminal group includes a nucleophilic functional group. Any convenient nucleophilic functional groups may be utilized at the terminals of the oligonucleotides to be conjugated. Nucleophilic functional groups of interest include, but are not limited to, hydroxyl, amino (e.g., primary or secondary amino), thiol, hydroxylamine, hydrazido and hydrazine. In some cases, a naturally occurring oligonucleotide terminal group, such a 5'-hydroxyl or a 3'-hydroxyl group, is coupled with the squarate reagent. In some embodiments, the terminal group is a 3'-amino terminal group. In some embodiments, the terminal group is a 5'-amino terminal group. A variety of methods, reagents and linkers are available that may be utilized to incorporate any convenient terminal functional groups of interest into the first and second oligonucleotides for coupling with the squarate reagent via the subject methods. For example, 3'-amino or 5'amino nucleosides are available that may be easily incorporated into an oligonucleotide of interest, e.g., via solid phase oligonucleotide synthesis.

In some embodiments of the method, the terminal functional group of the first and/or second oligonucleotide that is to be conjugated is a protected functional group, such as a protected nucleophilic group. In certain embodiments, the method further includes contacting the first and/or second oligonucleotide with a deprotection agent to produce a terminal amino group. In certain embodiments, the method further includes contacting the second oligonucleotide with a deprotection agent to produce the terminal amino group. In some cases, the terminal amino group of the oligonucleotide that is unmasked by deprotection may then be coupled with the monosquaramide or a squarate reagent, depending on a desired fragment coupling strategy.

In some embodiments, the activated first oligonucleotide that is produced in the subject method includes a terminal squarate monoamide group, e.g., a 3'-NH-squarate or a 5'-NH-squarate. As used herein, the terms "squaramide" and "monosquaramide" are meant to encompass not only the products of coupling of one or two amino terminal functional groups with a squarate reagent, but also the coupling(s) of any other convenient non-amino nucleophilic terminal group(s) (e.g., as described herein). As used herein, the term "monosquaramide" refers to a functional group having a cyclobutenedione core structure that is capable of forming one additional covalent bonds with a terminal oligo functional group at either the 3 or 4 position of the cyclobutenedione, e.g., the monosquaramide includes one labile leaving group at either the 3 or 4 position. In some cases, the monosquaramide may be referred to as a squarate/squaramide.

The coupling of a terminal nucleophilic group of an oligonucleotide to a monosquaramide may produce a squaramide linkage. FIG. 2 illustrates a monosquaramide containing oligonucleotide (3) that couples with a 5'amino terminal oligonucleotide (4) to produce a squaramide linked oligonucleotide (5). Aspects of the subject methods include conjugating the activated first oligonucleotide with a terminal of the second oligonucleotide via a squaramide linkage to produce a squaramide-linked oligonucleotide.

In some cases, a squaramide linkage may act as an internucleotide analog of the naturally occurring phosphate linkage. For example, as shown in scheme 1, squaric acid (and thus derivatives thereof) include a charged resonance structure that may be expected to mimic a phosphate group.

Scheme 1: Resonance structures of squaric acid and derivatives thereof

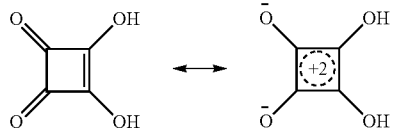

In some embodiments, a "squaramide" linkage for connecting a first and a second moiety is described by formula (II):

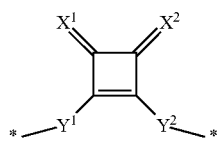

wherein $X^1$ and $X^2$ are each independently O or S; and $Y^1$ and $Y^2$ are each independently selected from the group consisting —NR—, —O—, —S—, —NRNR—, —C(O)NRNR— and —NR—O—, wherein each R is any suitable substituent. In some instances of formula (II), each R is independently selected from the group consisting of H, OH, alkoxy, substituted alkoxy, alkyl, and substituted alkyl.

In certain embodiments of formula (II), $Y^1$ and $Y^2$ are each —NR—. In certain embodiments of formula (II), $Y^1$ and $Y^2$ are each —NH—.

In certain embodiments of formula (II), $Y^1$ and $Y^2$ are each —N(OH)—. In certain embodiments of formula (II), one of $Y^1$ and $Y^2$ is —N(OH)—. In certain embodiments of formula (II), $Y^1$ and $Y^2$ are each —O—. In certain embodiments of formula (II), $Y^1$ and $Y^2$ are each —S—. In certain embodiments of formula (II), $Y^1$ and $Y^2$ are each —NRNR—. In certain embodiments of formula (II), $Y^1$ and $Y^2$ are each —NHNH—. In certain embodiments of formula (II), $Y^1$ and $Y^2$ are each —C(O)NRNR—. In certain embodiments of formula (II), $Y^1$ and $Y^2$ are each —C(O)NHNH—. In certain embodiments of formula (II), $Y^1$ and $Y^2$ are each —NRO—. In certain embodiments of formula (II), $Y^1$ and $Y^2$ are each —NHO—.

In certain embodiments of formula (II), $X^1$ is O and $X^2$ is S. In certain embodiments of formula (II), $X^1$ is S and $X^2$ is O. In certain embodiments of formula (II), $X^1$ and $X^2$ are both S. In certain embodiments of formula (II), $X^1$ and $X^2$ are both O. In some instances of formula (II), $X^1$ and $X^2$ are both O, but one or both of $X^1$ and $X^2$ are thionated during a subsequent downstream step of the subject methods.

In some embodiments, the squaramide-linked oligonucleotide is described by Formula (III):

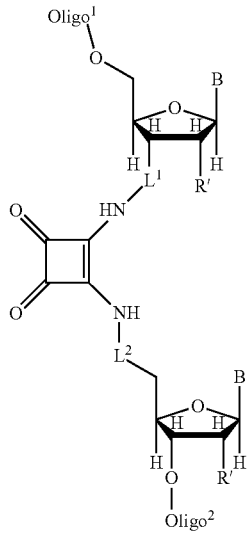

wherein:
Oligo$^1$ is the first oligonucleotide (minus the 3'-terminal nucleoside shown);
Oligo$^2$ is the second oligonucleotide (minus the 5'-terminal nucleoside shown);
each B is independently a nucleobase;
each R' is independently, H, OH, F, or OR, where R is an alkyl, a substituted alkyl or a hydroxyl protecting group; and
$L^1$ and $L^2$ are optional linkers (e.g., as defined herein).
In certain instances of formula (III), $L^1$ and $L^2$ are each a covalent bond. In some embodiments, when $L^1$ and $L^2$ are each a covalent bond (i.e., there are no linkers between the oligonucleotides and the squaramide linkage) the linkage is referred to as an internucleoside linkage. In certain instances of formula (III), each R' is selected from H and OH. In certain instances of formula (III), each R' is OH. In certain instances of formula (III), each R' is H.

Splint Oligonucleotide

Aspects of the disclosure include binding a first oligonucleotide and a second oligonucleotide to a splint oligonucleotide to conjugate the activated first oligonucleotide with a terminal of the second oligonucleotide via a squaramide linkage to produce a squaramide-linked oligonucleotide. As used herein, the term "splint oligonucleotide" refers to an oligonucleotide that has a first sequence of nucleotides complimentary to a region of the first oligonucleotide adjacent to the terminal and a second sequence of nucleotides complimentary to a region of the second oligonucleotide adjacent to the terminal. The splint oligonucleotide is capable of specifically binding both the first and second oligonucleotides to produce a complex, and thus bring the terminals of the first and second oligonucleotides into proximity. By bringing the terminals of the first and second oligonucleotide into proximity, the splint oligonucleotide increases the rate of the conjugation reaction via the intermediate squaramide activated oligonucleotide (e.g., as described herein). In some embodiments, when the splint oligonucleotide is not present, the first and second oligonucleotides do not conjugate. Any convenient methods and oligonucleotide splints of any convenient templated reaction or method may be adapted for use in the subject methods of conjugating oligonucleotides via squarate chemistry.

Figure 10:
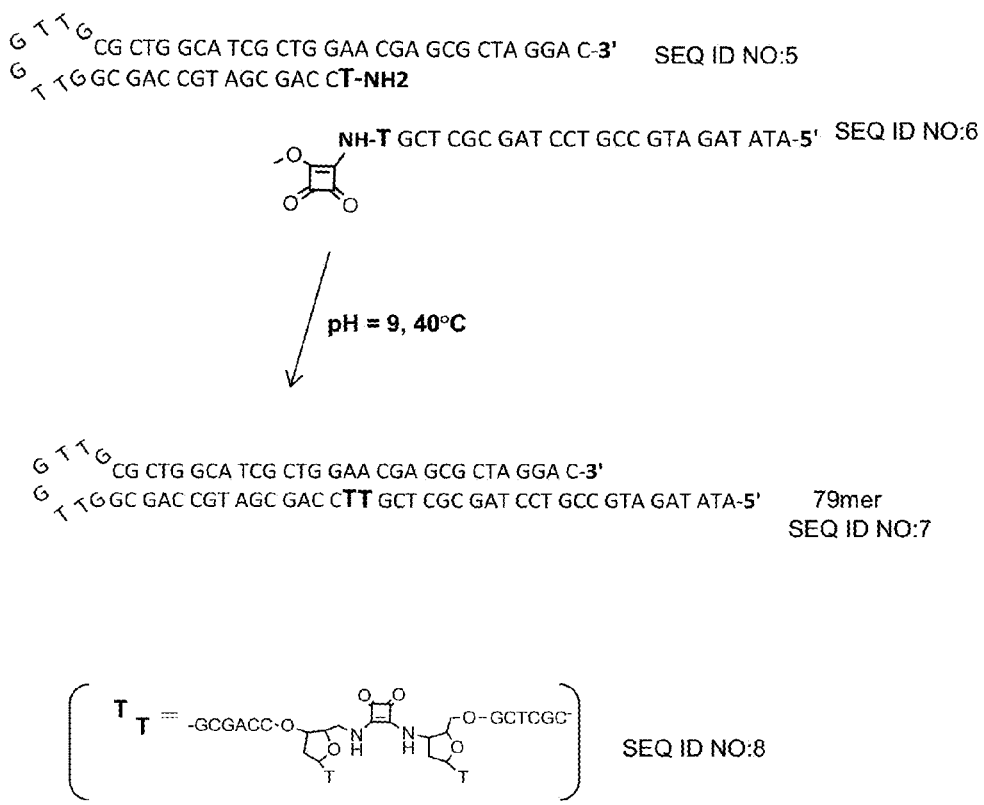
FIG. 10 illustrates the use of a secondary hairpin structure as an internal splint strand.

In some embodiments, the splint oligonucleotide is a distinct oligonucleotide that is separate from either the first and second oligonucleotides. In such cases, the splint oligonucleotide is capable of forming a termolecular complex with the first and second oligonucleotides. In certain embodiments, the splint oligonucleotide is part of the first oligonucleotide, i.e., an internal splint. In such cases, the splint oligonucleotide is capable of forming an intramolecular complex (e.g., a hairpin complex) with a region at the terminal of first oligonucleotide to produce an overlap sequence which specifically binds the second oligonucleotide. FIG. 10 illustrates the formation of a secondary hairpin structure via an internal splint strand, and the intermolecular binding and coupling of a second activated oligonucleotide that includes a terminal monosquaramide group to produce a squaramide linked oligonucleotide product.

Figure 5:
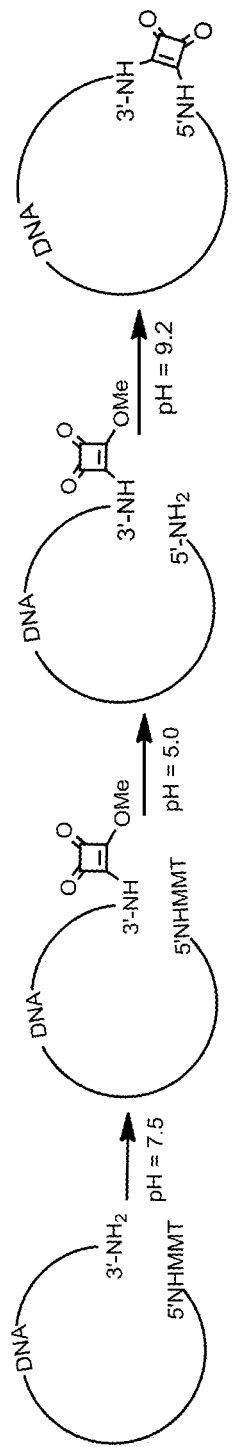
FIG. 5 shows a scheme for the cyclization of a 5' and 3' amino labeled DNA strand using MMT protecting groups and squarate chemistry.

In some embodiments, the method includes conjugating the terminals of a single oligonucleotide. In such cases, the binding of the single oligonucleotide to a splint oligonucleotide is optional. In some cases, the splint oligonucleotide includes first and second regions complementary to regions adjacent to both termini of a single oligonucleotide. FIG. 5 illustrates a method of cyclization of an oligonucleotide via a squaramide linkage, where first and second 5' and 3' amino labeled DNA oligonucleotides may be sequentially activated and coupled, using a protecting group strategy (e.g., MMT for amino terminal groups) and squarate coupling chemistry.

Methods

The activating and binding steps of the subject methods may be performed in any convenient order. The first and second oligonucleotides may be bound to the splint oligonucleotide before the activation of the first terminal group occurs. In certain embodiments of the method, the binding step is performed prior to the activating step. In some cases, contacting the resulting complex with a squarate reagent may directly produce the squaramide conjugated oligonucleotide. In such cases, activation of the first oligonucleotide may occur in situ to produce the intermediate squaramide group which is bound in the complex in proximity to the terminal of the second oligonucleotide and thus may quickly couple with the terminal of the second oligonucleotide.

In some embodiments of the method, the activating step is performed prior to the binding step. An activated first oligonucleotide (e.g., a monosquaramide terminal containing oligonucleotide) may be produced using any convenient methods. The activated oligonucleotide may be isolated and/or purified and/or characterized prior to use in any subsequent binding and/or coupling steps of the subject methods.

In the subject methods, any one of the first, second and splint oligonucleotides may be bound (e.g., covalently or non-covalently) to a support. In some embodiments, the splint oligonucleotide is bound to a support. Any convenient supports may be utilized in linking to the subject oligonucleotides. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. In some instances, the oligonucleotide is bound to an array.

Multi-Fragment Oligonucleotide Conjugations

Multiple fragments of a target oligonucleotide may be conjugated together to generate a longer oligonucleotide sequence. The fragments of a target synthesis may be selected depending on a variety of factors, such as the selection of desirable conjugation sites in a target sequence and fragments of desirable sizes that may be prepared via linear oligonucleotide synthesis. Any convenient fragment assembly strategies may be utilized in constructing a target oligonucleotide. Strategies that may be adapted for use in the subject methods include those utilized in protein synthesis via native chemical ligation, i.e., convergent fragment condensation strategies. Multiple fragments of a target oligonucleotide may be conjugated via any convenient strategies according to the subject methods. Conjugation of multiple fragment may be achieved sequentially, via a convergent conjugation strategy, or simultaneously using multiple splint oligonucleotides in a single reaction mixture. In some cases, 2 or more distinct splint oligonucleotides, such as 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 200 or more, 300 or more, 400 or more, 500 or more distinct splint oligonucleotides may be used in the preparation of a target oligonucleotide.

In some cases, the oligonucleotides prepared according to the subject methods may include two or more squaramide linkages, such as 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 200 or more, 300 or more, 400 or more, 500 or more, or even more squaramide linkages.

In some embodiments, the method further includes: dissociating the squaramide-linked oligonucleotide from the splint oligonucleotide; and binding the squaramide-linked oligonucleotide to a second splint oligonucleotide that includes a region complementary to a third oligonucleotide; and activating a terminal of the squaramide-linked oligonucleotide using a squarate reagent. The dissociating step and the binding step may be performed in any convenient order. It is understood that the subject method may be elaborated to include multiple binding and/or dissociation steps (e.g., as described herein) to construct a oligonucleotide via a multiple fragment synthesis. In some embodiments, one or more splint oligonucleotides are immobilized on a support (e.g., an array). Dissociation may be achieved using any convenient methods. In some cases, dissociation of a complex including a splint oligonucleotide is achieved through use of a displacement member that competes for binding to the splint oligonucleotide or to its complementary oligonucleotide fragment.

In some embodiments, the method further includes: activating either the second terminal of the first oligonucleotide or a terminal of a third oligonucleotide with a squarate reagent; and binding the first oligonucleotide and the third oligonucleotide to a second splint oligonucleotide; to conjugate the first and third oligonucleotides via a squaramide linkage to produce a squaramide-linked oligonucleotide that comprises two or more squaramide linkages. In certain embodiments of the method, the first oligonucleotide is bound to the second and third oligonucleotides simultaneously. In certain embodiments of the method, the first oligonucleotide is bound to the second and third oligonucleotides sequentially.

Amplification

The squaramide-linked oligonucleotides produced according to the methods described herein may be amplified using any convenient methods, e.g., using a DNA polymerase. Amplification methods of interest include, but are not limited to, PCR methods. In some embodiments, the method further includes amplifying the squaramide-linked oligonucleotide using a DNA polymerase. In certain instances, the amplifying includes amplifying a sequence of the oligonucleotide that includes a squaramide linkage.

Compositions

Aspects of the invention include oligonucleotides and compositions thereof. Any convenient oligonucleotide that includes a squaramide linkage may be prepared according to the subject methods (e.g., as described herein). In certain instances, the subject oligonucleotides are prepared using the subject methods on a solid support. In certain cases, the subject oligonucleotides are prepared using the subject methods in solution phase. The oligonucleotides may be prepared at any convenient scale. In some instances, the oligonucleotides are prepared at a 0.1 umol scale or larger, such as a 0.5 umol scale or larger, 1 umol scale or larger, 2 umol scale or larger, 3 umol scale or larger, 5 umol scale or larger, 10 umol scale or larger, 100 umol scale or larger, 1 mmol scale or larger, 3 mmol scale or larger, 10 mmol scale or larger, 100 mmol scale or larger, or even larger.

In some embodiments, the oligonucleotide, includes: a oligonucleotide sequence including 40 or more nucleosides (such as, 50 or more, 60 or more, 70 or more, 80 or more, 90 or more, 100 or more, 200 or more, 300 or more, 400 or more, 500 or more, 600 or more, 700 or more, 800 or more, 900 or more, 1000 or more, 1500 or more, 2000 or more, 3000 or more, 4000 or more, 5000 or more, 6000 or more, 7000 or more, 8000 or more, 9000 or more, 10,000 or more, 10,000 or more, 10,000 or more, 10,000 or more, 10,000 or more, 10,000 or more, 10,000 or more, 10,000 or more, 10,000 or more, 10,000 or more, or even more nucleosides); and a squaramide internucleoside linkage.

In certain embodiments, the oligonucleotide has a sequence comprising 1000 or more nucleosides (e.g., 1500 or more, 2000 or more, 5000 or more, etc.), and a plurality of squaramide internucleoside linkages. In certain cases, the oligonucleotide includes sequence fragments of 100 or less nucleosides between adjacent squaramide internucleoside linkages, such as 90 or less nucleosides, 80 or less nucleosides, 70 or less nucleosides, 60 or less nucleosides, 50 or less nucleosides, or even 40 or less nucleosides between adjacent squaramide internucleoside linkages.

In certain embodiments, the oligonucleotide includes 2 or more squaramide linkages, such as 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 200 or more, 300 or more, 400 or more, 500 or more, or even more squaramide linkages. In certain embodiments, the 2 or more squaramide linkages are each internucleoside linkages.

In some embodiments, the oligonucleotide is bound to an array. In certain cases, the oligonucleotide is covalently bound to the array, e.g., via a terminal covalent linker. In some instances, the oligonucleotide is non-covalently bound to the array, e.g., via hybridization to an immobilized oligonucleotide probe. In certain embodiments, the oligonucleotide is cyclic. Cyclic oligonucleotides may find use in a variety of applications such as in circular DNA amplification, e.g., rolling circle amplification.

Any of the subject oligonucleotides may be copied (e.g., amplified as described herein) using any convenient methods. Aspects of the disclosure include a composition, including: a first oligonucleotide including at least one squaramide internucleoside linkage; and a second oligonucleotide that comprises a sequence complementary to the first oligonucleotide, wherein the second oligonucleotide does not comprise a squaramide linkage. The second sequence may be produced using any convenient methods, e.g., via the action of a DNA polymerase on the first oligonucleotide. In certain cases, the second oligonucleotide is a DNA polymerase amplification product. In some cases, the composition further includes a DNA polymerase. In certain embodiments of the composition, the first oligonucleotide includes 300 or more nucleosides.

Kits

Aspects of the invention further include kits for use in practicing the subject methods and compositions. The compositions of the invention can be included as reagents in kits either as starting materials or provided for use in, for example, the methodologies described above.

A kit may include a squaramide linked oligonucleotide (e.g., as described herein) and/or an activated oligonucleotide (e.g., as described herein); and one or more components selected from a dye, a tandem dye, a specific binding member or a conjugate thereof, a cell, a support, an biocompatible aqueous elution buffer, a hybridization buffer, a DNA polymerase, other DNA amplification reagents and instructions for use.

In certain embodiments, the kit finds use in the preparation and amplification of long oligonucleotide sequences. As such, in some instances, the kit includes one or more components suitable for amplifying DNA or RNA, such as a DNA polymerase and/or one or more components of any convenient DNA amplification system. The one or more additional components may be provided in separate containers (e.g., separate tubes, bottles, or wells in a multi-well strip or plate).

In certain aspects, the kit may further include reagents for hybridization and/or modification of oligonucleotides. Examples of said reagents include buffers for e.g., reconstitution and dilution of the first and second oligonucleotides, buffers for hybridization, wash buffers, control oligos, fluorescent dyes for oligonucleotide detection and combinations thereof. A variety of other components that find use in the subject methods familiar to the skilled artisan are within the scope of the subject kits.

The composition may be provided in a liquid composition, such as any suitable buffer. Alternatively, the composition may be provided in a dry composition (e.g., may be lyophilized), and the kit may optionally include one or more buffers for reconstituting the dry composition. In certain aspects, the kit may include aliquots of the composition provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The methods, compositions, and kits as described herein may find use in a variety of applications, including diagnostic, therapeutic and research applications, in which the synthesis of an oligonucleotide of interest is desirable. Target oligonucleotides of interest find use in a variety of applications, e.g., as therapeutic agents or as diagnostic agents.

In some cases, the methods and compositions find use in making oligonucleotides of between 500 and 10,000 bases in length, where the oligonucleotide may be prepared as a single strand or as a duplex and may be easily modified as desired to include one or more sequence modifications or nucleotide analogs. In some cases, the methods and compositions find use in making relatively large quantities of oligonucleotides of a desired length.

The following examples are offered by way of illustration and not by way of limitation.

EXAMPLES

Example 1

Squarate Mediated Conjugation of Two Non-Complimentary DNA Strands with RNA Using an RNA Splint In this example the two non-complementary strands were coupled. One strand was a DNA 28 mer with a 3' C7 amine terminated linker, the other strand was a RNA 20 mer with a 5' labeled amino linker. This coupling of two non-complementary strands was achieved through the use of a splint strand. In this example, a RNA 21 mer with half the sequence complimentary to the 3' end of the DNA and the other part of the RNA 20 mer complimentary to the 5' amino terminated RNA 20 mer was prepared. The mono squarate is prepared first (see FIG. 1). The 5' amino RNA was converted into the mono squarate with yields exceeding 95%. Ultrafiltration of the reaction mixture, on a 2K membrane, removes the remaining squarate reagent and other small molecules. This mono squarate was lyophilized and stored in a freezer (−20° C.) for at least two years without degradation and or loss of conjugation activity. The mono squarate of the 5'-C6 amino labeled RNA was mixed with the RNA splint strand along with the DNA 28 mer labeled with the C7 amino linker at the 3' end in approximately equal amounts (10-200 nM). The pH was brought to 9.2 by the addition of 100 mM Sodium Borate. The resulting mixture was allowed to stand at 22° C. for 17 hours. Analysis of the reaction mixture by LCMS-ES showed that the coupling reaction had gone to completion to produce the expected 48 mer DNA/RNA conjugate in >90% yield based on remaining single strands. This squarate conjugation provides for the construction of long oligonucleotides via coupling of amino linker labeled, 5' and/or 3' DNA and/or RNA with each other via a squaramide linkage using a splint strand to template the two strands together during conjugation. Further conjugations can be performed on the product and repeated over and over again using DNA/RNA labeled with amino linkers on both 5' and 3' ends.

Example 2

Coupling of Two Strands of Amine Modified DNA Using Squarate Chemistry (FIG. 2)

The squaramide linkage serves as a mimic for the natural phosphodiester coupling. The 5'NH₂ and 3'NH₂ derivatives of dT are commercially available. This limitation in amidite type does not prevent long DNA assembly or related PCR experiments as two dT's together in a sequence are common.

Using standard solid phase synthesis techniques three DNA strands were prepared at 1 µmole scale. These were the 5' segment: 5'-HO-dA-DNA23 mer-dT-NH₂-3', the 3' segment: 5'NH₂-dT-DNA35 mer-dT-OH-3' and the 28 mer DNA splint strand:

```
    (SEQ ID NO: 1 and SEQ ID NO: 2, respectively)
5'-ATA TAG ATG CCG TCC TAG CGC TCG T-3'-

NH-SQ-NH-5'-TC CAG CGA TGC CAG TTG GGC ACA

GGA AAG ATA CTT-3'

3'-C AGG ATC GCG AGC A-----------------------

AG GTC GCT ACG GTC-5'
```

(where NH-SQ-NH represents a squaramide linkage depicted in the last structure shown in FIG. 2).

A solution (1-200 nM) of 5'-HO-dA-DNA23 mer-dT-NH₂-3' was converted to the mono squarate at pH 7.2 (see FIG. 2) by treatment with excess dimethoxysquarate dissolved in DMSO. The excess dimethoxy squarate used to make the mono squarate was easily removed by NAP 10 column or Amicon 3K molecular weight cut off spin filters. The resulting mono squarate/squaramide was then added to an equivalent of the splint strand and the 5'NH₂-dT-DNA34 mer (approx. 10-200 nM). The solution pH was then raised from 7.2 to 9.2 by addition of a sodium borate solution to initiate the ligation reaction. The mixture was then kept at 40° C. for 20 minutes. LCMS analysis of the reaction showed that the expected 60 mer was formed in approximately 90% yield based on remaining amounts of the single strands.

Alternatively, a solution (approximately 200 nM) of 5'-OH-DNA24 mer-3'-dT-NH₂, 5'-NH₂-dT-DNA34 mer-3'-OH and 28 mer splint strand was prepared in approximately 100 mM sodium borate. To this solution was added a slight excess of dimethoxysquarate dissolved in DMSO. LCMS analysis of the reaction after 1 hour showed that the expected DNA product was formed in good yield.

The splint strands depicted below were utilized in the following examples.

```
DNA20mer splint:
                                    (SEQ ID NO: 3)
3'-ATC GCG AGC AAG GTC GCT AC-5'

(A,C,G,T = DNA monomers)

RNA20mer splint:
                                    (SEQ ID NO: 4)
3'-auc gcg agc aag guc gcu ac-5'

(a,c,g,u = RNA monomers)
```

The 5'-HO-dA-DNA23 mer-dT-NH₂-3' mono squarate (see FIG. 2), was added to an equivalent of the splint strand (either 20 mer DNA or 20 mer RNA) and the 5'NH₂-dT-DNA34 mer. The solution pH was then raised from 7.2 to 9.2 by addition of a sodium borate solution (pH 9 sodium phosphate also worked) to initiate the ligation reaction. The mixtures were allowed to stand at room temperature for at least 30 minutes. LCMS analysis of the reaction showed that the expected 60 mer was formed in approximately 90% yield based on remaining amounts of the single strands from both DNA and RNA 21 mer splint strands.

In another experiment the 20 mer DNA splint was used to couple the 5' segment, 5'-HO-dA-DNA23 mer-dT-NH$_2$-3', to the 3' segment, 5'NH$_2$-dT-DNA33 mer-dT-OH-3' without first activating the 5' segment to the mono squarate. In this experiment a mixture (approx. 1 to 1 to 1) of the three strands; 21 mer DNA splint, the 5'-HO-dA-DNA23 mer-dT-NH$_2$-3' and the, 5'NH$_2$-dT-DNA33 mer-dT-OH— was mixed in pH=9 buffer. To this mixture was added an excess of dimethoxy squarate dissolved in DMSO. LCMS analysis of the reaction mixture after 30 minutes at room temperature showed that the expected 60 mer dimer had formed in good yield.

In another experiment, the 20 mer DNA splint was used to couple the 5' segment, 5'-HO-dA-DNA23 mer-dT-NH$_2$-3', to the 3' segment, 5'NH$_2$-dT-DNA66 mer-dT-OH-3'. An equivalent of the DNA 20 mer splint strand was added to an approximately 1 to 1 ratio of the 5'-HO-dA-DNA23 mer-dT-NH$_2$-3' mono squarate (see FIG. 2), and the 5'NH$_2$-dT-DNA66 mer-dT-NH$_2$-3' at pH=9.2. The mixtures were allowed to stand at room temperature for at least 30 minutes. LCMS analysis of the reaction showed that the expected 93 mer was formed in approximately 90% yield based on remaining amounts of the full length single strands.

Example 3

Multi-Fragment Synthesis of Long Oligonucleotides

Figure 3:
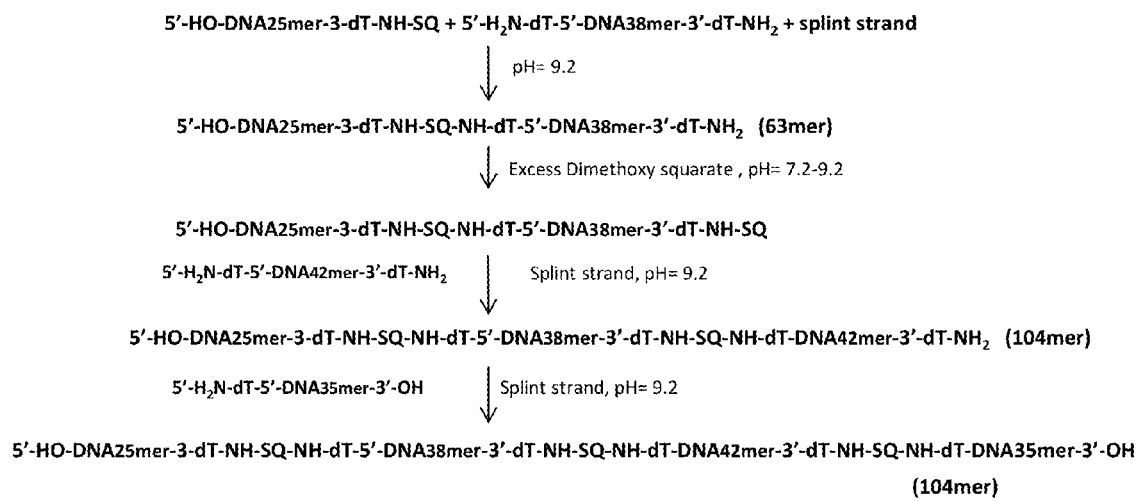
FIG. 3 illustrates a general reaction scheme for the synthesis of long oligonucleotides.

The squarate chemistry can be used to attach more than two oligonucleotides together. FIG. 3 shows a general reaction scheme that finds use in the synthesis of long oligonucleotides. The ligation sequence starts with a 5'OH-DNA-3'NH$_2$ species and is elongated in sequential addition of 5'-NH$_2$-DNA-NH$_2$-3'with a final capping of 5'-NH$_2$-DNA-3'OH. In the reaction sequence shown in FIG. 3, a 140 mer is formed that contains three squaramide (SQ) linkages.

The DNA24 mer-3'dT-NH-SQ (10-200nM) described in the previous example was mixed with approximately 1 equivalent of the 5'NH$_2$-dT-DNA35 mer-3'dT-NH$_2$ and DNA20 mer splint strand at pH=9.2, as shown in FIG. 3. The mixture was allowed to stand at 22° C. for 16 hours. LCMS analysis of a desalted solution showed that the 25 mer and 38 mer had coupled in >90% yield based on remaining single strands to give the expected DNA63 mer with a squaramide linkage and 3'-dT-NH$_2$. This material was isolated by anion exchange chromatography and used in the next coupling.

The isolated DNA63 mer squaramide with 3'dT-NH$_2$ was converted to the 3'dT-NH-SQ. After removal of the excess squaramide (Amicon 3K molecular weight cut off spin filters), the retentate was then treated with an approximately equal molar amount of the DNA splint stand and a 1.5 molar excess of the next strand to be coupled, 5'-NH$_2$-dT-DNA 40 mer-3'-dT-NH$_2$. After 16 hours at 22° C. LCMS analysis showed that the expected 105 mer (di squaramide)-3'-dTNH$_2$ was formed in excellent yield. The product was isolated by anion exchange chromatography and used in the next coupling.

The isolated DNA105 mer, bis-squaramide with 3'dT-NH$_2$ was converted to the 3'dT-NH-SQ. After removal of the excess squaramide (Amicon 3K molecular weight cut off spin filters),the retentate was then treated with an approximately equal molar amount of the DNA splint stand and an excess of the next strand to be coupled, 5'-NH$_2$-dT-DNA 34 mer-3'-OH. After approximately 16 hours at 22° C. LCMS analysis showed that the expected 140 mer (tri squaramide)-3'-OH was formed in >95% based on remaining 105 mer (di squaramide). The product was isolated by anion exchange chromatography. The isolated material was analyzed by LCMS and gave an observed MW=43, 147.0, calculated MW=43,146.3.

This general method is adapted to include coupling of large blocks of squaramide coupled oligos to each other, e.g., via a linear or convergent multi-fragment synthesis.

For example, a DNA strand (containing multiple squaramide linkages) with a 3'-NH-mono squarate/squaramide group is coupled to a 5'NH$_2$-DNA strand (also with multiple squarate linkages). The synthesis method described in FIG. 4 is used to make the 5'-DNAx-3'-NH-SQ compounds. Building the middle blocks requires protecting the 5'-NH$_2$ group so the 3' NH$_2$ group can form the mono squarate/squaramide intermediate. This is done by keeping the mono methoxytrityl (MMT) protecting group (or other protecting group) on the NH$_2$ dT(on an oligo also containing the 3' NH$_2$ group) on the 5'end of the oligonucleotide until this 5'-dT-NH$_2$ is coupled to another block with a 3'-NH-squarate. This block coupling concept is shown in FIG. 4B. An example of this type of convergent synthesis was demonstrated as follows.

A solution (approximately 100 nM) of a 5'OH-DNA48 mer-3'dT-NH SQ, 5'NH$_2$-dT-DNA36 mer-3'-dT-NH$_2$ and 20 mer DNA splint strand was prepared in 50 mM sodium borate, pH=9.2. LCMS analysis of the reaction mixture after 8 hours at 22° C. showed that the expected DNA87 mer mono squaramide with 3'dT-NH$_2$ was formed in good yield. The product was isolated by anion exchange chromatography. A solution (approximately 100 nM) of a 5'NH$_2$-dT-DNA40 mer-3'-dT-NH$_2$, 5'SQ-NH-dT-DNA67 mer-3'-OH and 20 mer DNA splint strand was prepared in 50 mM sodium borate, pH=9.2. LCMS analysis of the reaction mixture after 8 hours at 22° C. showed that the expected DNA10 mer mono squaramide with 5'dT-NH$_2$ (3'OH) was formed in good yield. The product was isolated by anion exchange chromatography.

The 5'OH-DNA86 mer-3'dT-NH$_2$ was cleanly converted to the mono squarate by treatment with dimethoxysquarate at pH 9.2 at room temperature after 30minutes. After the excess dimethoxysquarate was removed (Amicon 3K membrane, see earlier examples) The 5'OH-DNA86 mer-3'dT-NH-SQ was mixed with the 5'-NH$_2$-dT-DNA109 mer-3'-OH along with an equivalent of a DNA22 mer splint strand. The solution was made 50 mM in sodium borate and warmed to approximately 40° C. for 36 hours. Analysis of the reaction mixture by LCMS showed that the expected 197 mer observed MW=60,495.98, calc MW=60496.60.

In summary, these methods of chemically ligating oligonucleotide strands together by the squaramide phosphodiester mimic is used to make long oligonucleotides (DNA/RNA/modified and combinations of all) of greater length than current large scale sequential synthesis methods. The coupling only involves pH control. The first step can occur at neutral pH, the second at pH of 9 (sodium borate solution, pH=9.2 or other non-amine buffer at the approximate pH). For faster mono-squaramide formation the reaction can be done at the higher pH (in sodium borate for example). The method uses an inexpensive small molecule that is easily removed from the oligonucleotide mixture.

Example 4

Immobilization of the Splint Strand on a Solid Support

A way to automate this type of synthesis method is to covalently attach the splint strand to a solid support. The following general protocol was adapted for use in the preparation of long oligonucleotides.
1. An amino labeled resin (Tosoh Toyopearl AF-Amino-650M) is placed in a beaker (a small synthesis column can also be used). The amino labeled support is washed with the conjugation buffer, pH 7-9.2.
2. A solution of dimethoxysquarate is prepared by dissolving excess reagent in DMSO and then adding this solution to the pH7-9.2 buffer used for the conjugation to the support.
3. The amino resin is then suspended in the dimethoxysquarate soluton. After approximately one hour the excess dimethoxysquarate is washed (water/DMSO) from the support with water until no UV absorbance due to unreacted dimethoxysquarate is observed.
4. A solution of the splint 5'NH$_2$—C6-HEG-DNA /RNA-3' is prepared in sodium Borate buffer at pH 9.2.
5. The splint strand solution is added to the support and the mixture allowed to stand at room temperature for two and a half hours.
6. Wash the support with sodium phosphate buffer, pH 7, in 1M NaCl to remove any remaining splint strand. Follow removal of splint strand using UV spectroscopy at A260 nm.
7. Treat the resin with an excess of amino ethanol in a mixture of DMSO/100 mM Borate in order to quench any remaining mono squarate that didn't reaction with the splint strand.
8. An approximately 1:1 mixture of the 5'NH$_2$-dT-DNA48 mer with 3'SQ-NH-dT 67 mer is stood at room temperature (approx. 25° C.) for two hours.
9. Rinse the resin with 100 mM sodium phosphate (pH approximately 7-8) until the washes have no UV absorbance (A260nm).
10. Heat the support (in 100 mM sodium phosphate, pH-7-8) at 65° C. and filter.
11. LCMS analysis of this solution show the expected 117 mer along with some unreacted single strands.
12. Repeat heating and washing steps until no further UV absorbance is seen in the washes.
13. The coupling cycle iss repeated (excess of 5'NH$_2$-dT 48 mer) with this same resin. The final wash produces the expected 117 mer with only some of the excess 49 mer present. 15. This procedure can be expanded to produce multiple squaramide coupled oligonucleotides. In this application the 3'SQ-NH-DNA would be treated with 5'-NH$_2$-dT-DNA/RNA-3'NH$_2$ using the appropriate splint strand attached to the support. Upon removal of the coupled strand the product (with 3'dT-NH$_2$) was converted to the mono squaramide and the cycle repeated with appropriate splint strands bound to a solid support until the desired length is achieved.

Example 5

Preparation of Cyclic DNA

Another application of this conjugation/ligation procedure is to make cyclic DNA, e.g., that's suitable for using in rolling circle replication. FIG. 5 shows an example of how this is accomplished. Intramolecular coupling may occur with or without the appropriate splint strand.

A DNA 45 mer with 3'-NH$_2$-dT-DNA-5'-dTNH-MMT was synthesized using standard solid phase synthesis techniques. The MMT protecting group was left on and the deprotection was done in concentrated ammonia at 55° C. for 20 hours.

LCMS analysis showed that the MMT group was still present. A sample of this material was washed 4 times with 50 mM sodium borate (pH=9.2) solution in an Amicon 3K molecular weight cutoff spin filter. The resulting solution (in 50 mM sodium borate) was treated with excess dimethyl squarate/DMSO. After approximately ten minutes the reaction mixture was desalted using an Amicon 3K molecular weight cut off spin filter. LCMS analysis of the resulting solution showed that the desired 5'MMT-NH-dT-DNA-3dT-NH-SQ had formed in near quantitative yield. This mixture, approximately 300 uL was treated with 20 uL of a 10% acetic acid aqueous solution. After approximately two minutes the reaction was washed with water and 50 mM sodium borate using an Amicon 3K molecular weight cut off spin filter. LCMS analysis of this solution showed that the MMT group had been completely removed giving the 5-NH$_2$-dT-DNA43 mer-3'NH-dT-SQ.

A solution (approx. 30 nM) of the 5'-NH$_2$-dT-DNA43 mer-3'-dT-NH-SQ in approximately 100 mM sodium borate was allowed to stand at 15° C. for 48 hours. The reaction was desalted using an Amicon 3K molecular weight cut off spin filter. LCMS analysis of the resulting solution showed that the cyclic product had been formed in near quantitative yield. Cyclization at higher temperatures gave lower yields of cyclized DNA with larger amounts of the hydrolysis product of the 3'-dT-NH-SQ.

Example 6

Synthesis of Long Oligonucleotide Duplexes

Figure 6:
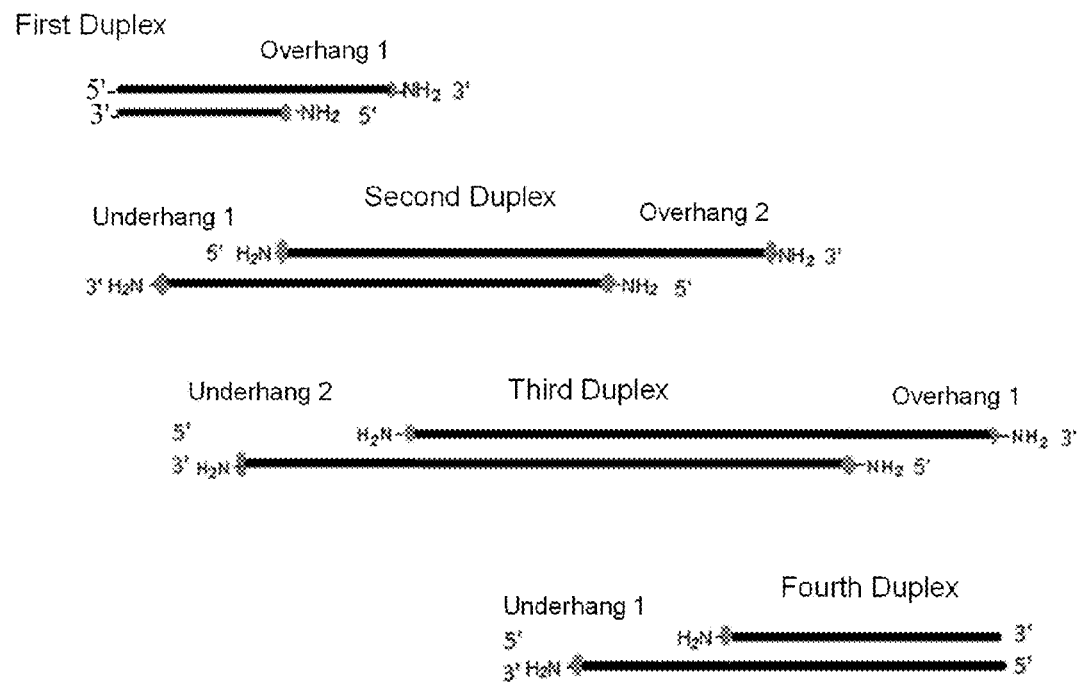
FIG. 6 illustrates four duplexes with over hanging and under hanging regions that find use in the preparation of a long oligonucleotide duplex.
Figure 7:
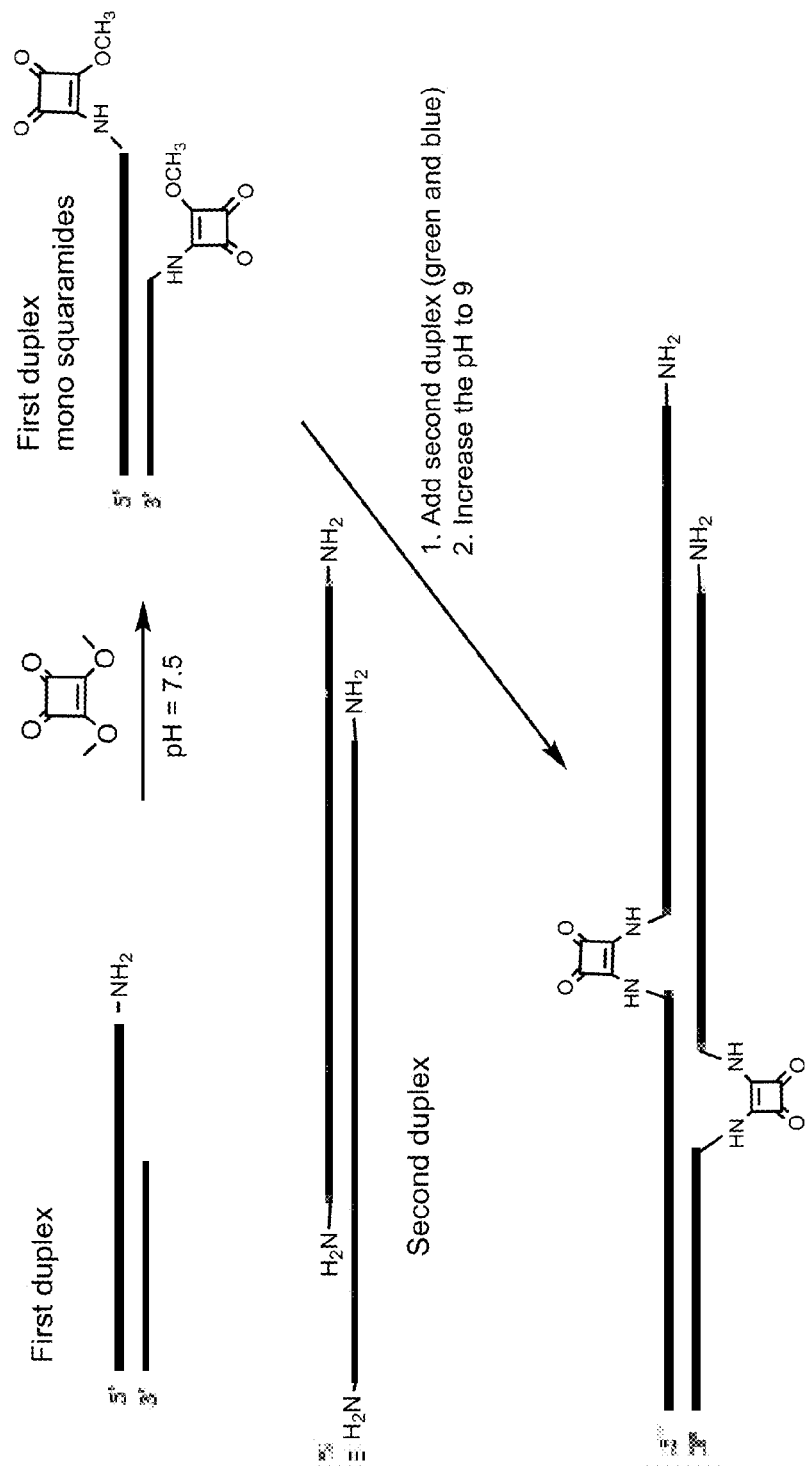
FIG. 7 illustrates an exemplary duplex DNA squaramide coupling scheme.
Figure 8:
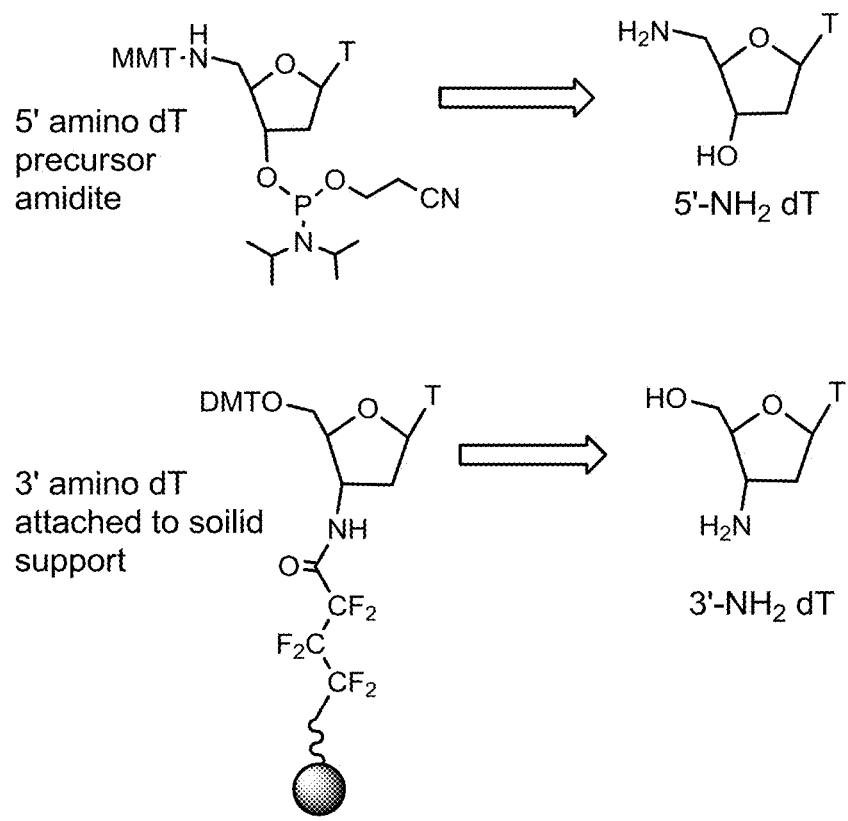
FIG. 8 illustrates an exemplary method for introducing $NH_2$ groups at the terminal of oligonucleotide fragments via 5' and 3' amino dT monomers. The 5'MMT amino-phosphoramidite and the support loaded 3'amino dT are commercially available.

Synthesize and purify the eight single strands (50 to 80 mer's DNA) and make the four duplexes illustrated in FIGS. 6 and 7. The NH$_2$ groups shown at the ends of the duplexes are produced from the 5' and 3' amino dT monomers as shown in FIG. 8. The 5'MMT amino-phosphoramidite and the support loaded 3'amino dT are commercially available.

The first Duplex has a dT 5' NH$_2$ on the shorter strand and a dT 3'NH$_2$ on the overhang end; —NH$_2$ group in FIG. 6. The overhang 1 sequence is complimentary to the underhanging 1 sequence in the second Duplex. The second Duplex has over/under-hangs on both ends of the duplex with the complimentary sections in the middle. The underhang 1 sequence is complimentary to the overhang 1 of the first duplex. The length of the overhang ends is expected to be 10-20 nucleotide range. The third Duplex is similar to the second duplex, with over/under-hangs on both ends of the duplex, also four of the —NH$_2$ dT nucleosides on each end. The underhang 2 end is complimentary to the overhang 2 end of the second duplex and the overhang 1 is complimentary to the under-hang 1 in the fourth duplex. The overhang 1 is also complimentary to the under-hang 1 in the second duplex, this way the duplex can continue to grow by repeating the second and third strand additions until the desired length then capped with the fourth duplex.

Synthesis Cycle, see FIG. 7: To the first duplex (blunt end duplex) dissolved in pH 8 buffer add an approx. 40 fold excess of dimethoxy-squarate dissolved in DMSO. The reaction can be heated to increase the reaction rate. The di-squaramide formation is determined by LCMS analysis. Remove the excess methoxy squarate and other small molecules using a 3K Amicon Spin filter(s), and spin at least 4× against water (until no UV remains in the permeate). Add approximately 1.1 equivalents of the second duplex (with overlap ends) to the retentate from the 3K spin filter step. Raise the mixture's pH to 9. The coupling reaction's progress (up to approx. 150 mers) is observed by LCMS analysis.

Figure 9:
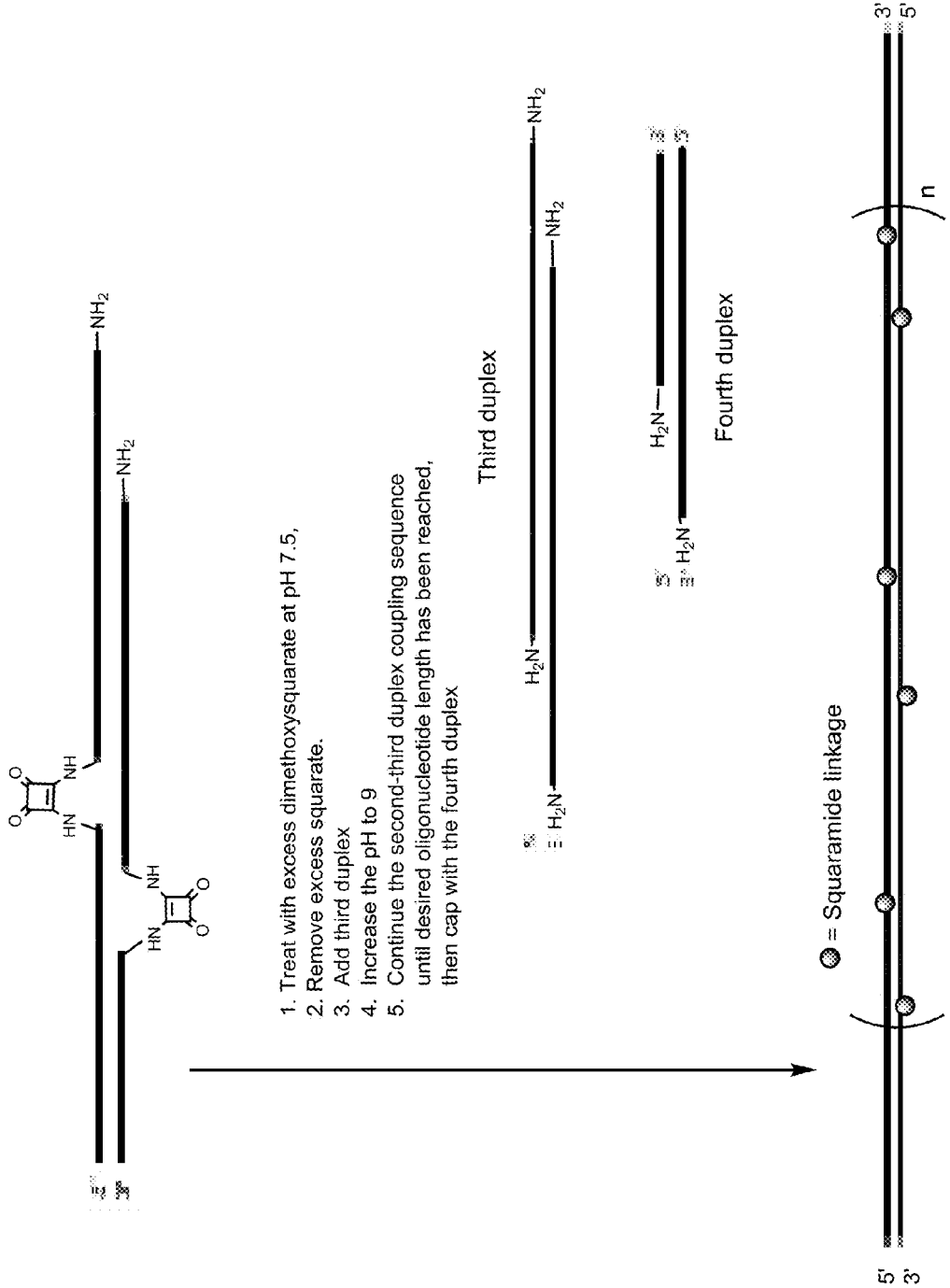
FIG. 9 illustrates coupling of the third and fourth duplexes including the second-third repeating squaramide coupling in the synthesis of duplex DNA.

Continue the cycles with the Third and Fourth duplexes, see FIG. 9. Alternatively, instead of capping the product duplex with the Fourth duplex, one can add the Second duplex to the Third (due to the designed overlapping regions shown by the complimentary segments), and repeat over and over again until the desired length is reached then add the fourth duplex to complete the large duplex synthesis.

An example of duplex synthesis shown in FIGS. 7 and 9 was successfully performed. The first duplex (FIG. 7) was made by mixing equal molar amounts of 5'-OH-DNA52 mer with 3'dT-NH$_2$ with its complimentary strand, a 3'-OH-DNA41 mer-5'-dT-NH$_2$. This solution was brought to 50 mM in sodium borate and an excess of dimethoxysquarate dissolved in DMSO. After approximately 30 minutes the excess squarate reagent was removed by washing with water in Amicon 3K molecular weight cutoff spin filters. The resulting bis squaramide duplex was used in the next coupling. The second duplex was made by mixing approximately equal molar amounts of the 5'-NH$_2$-dT-DNA52 mer-3'dT-NH$_2$ and its complimentary strand, a 3'NH$_2$-dT-51 mer-5'-dT-NH$_2$ then bringing the combined solution to 50 mM sodium borate (pH=9.2). After 3 hours at room temperature the reaction was analyzed by LCMS which showed that the expected new duplex (107 mer/96 mer) had formed in good yield. The new duplex was isolated by anion exchange chromatography.

This new duplex solution was brought to 50 mM in sodium borate and an excess of dimethoxysquarate dissolved in DMSO. After approximately 30 minutes the excess squarate reagent was removed by washing with water in Amicon 3K molecular weight cutoff spin filters. LCMS analysis confirmed that both of the dT-NH$_2$ ends (3' and 5') had been converted to the desired mono squarates.

The third duplex (FIG. 9) was prepared by mixing approximately equal molar amounts of the 5'-NH$_2$-dT-DNA56 mer-3'dT-NH$_2$ and its complimentary strand, a 3'NH$_2$-dT-57 mer-5'-dT-NH$_2$ then bringing the combined solution to 50 mM sodium borate (pH=9.2). After 3 hours at room temperature the reaction was analyzed by LCMS. The UV chromatograph of the analysis showed that a later eluting large broad peak characteristic of a larger duplex. This larger duplex (165 mer/155 mer di squaramide) was not observed by MS due to the difficulty in denaturing such a large DNA duplex. The MS signals for the starting 107 mer/96 mer duplex were not observed either.

Example 7

Hairpin Self-Splinting Based Addition of a Complementary Strand Using Squarate Chemistry Coupling The secondary structure within one of the coupling strands is used to direct the attachment of the other strand. In this example, the mono squarate/squaramide of the 3'-dT-NH$_2$ containing strand was premade before coupling (FIG. 10). Alternatively, as with the other examples, the two strands can also be mixed together and then coupled by adding the appropriate amount of dimethoxysquarate at pH=9. A 3'-NH$_2$-dT-DNA24 mer-3'-OH was converted into the mono squarate as described above. The 3'-SQ-NH-dT-DNA24 mer-3'OH was mixed with an approximately equal molar amount of a hairpin DNA, 5'NH$_2$-dT-DNA53 mer-3'OH in 50 mM sodium borate (pH=9.2) at 40° C. for 1.5 hours. LCMS analysis showed that the expected hairpin product, DNA78 mer mono squaramide was formed in high yield.

In a similar reaction an aqueous solution of 3'SQ-NH-dT-DNA48 mer-3'-OH was mixed with an approximately equal molar amount of a hairpin DNA, 5'NH$_2$-dT-DNA53 mer-3'OH in 50 mM sodium borate (pH=9.2) at room temperature for 24 hours. LCMS analysis showed that the expected hairpin product, DNA103 mer was formed in high yield.

Example 8

The use of secondary and or tertiary structure formed between oligonucleotides (RNA and or DNA) is used to couple strands together using this squarate methodology. This can be at a stem section (see Example 7), a loop or bulge in the secondary structure formed between the oligonucleotides being coupled. This would include internal coupling between one strand (see Example 5, FIG. 5), coupling two strands and coupling of multiple strands that when mixed together form secondary and or tertiary structure with each other that place the desired ends in a position to be ligated using squarate coupling chemistry.

Two RNA strands, one with a 3'dT-NH$_2$ and the other with a 5'dTNH$_2$, were synthesized using TC and TBDMS solid phase synthesis and deprotection techniques. The two strands were designed to use the CRISPR RNA secondary/tertiary structure to direct the ligation in an area that based on structure data does not appear to interfere with the CAS9 function.

Figure 11:
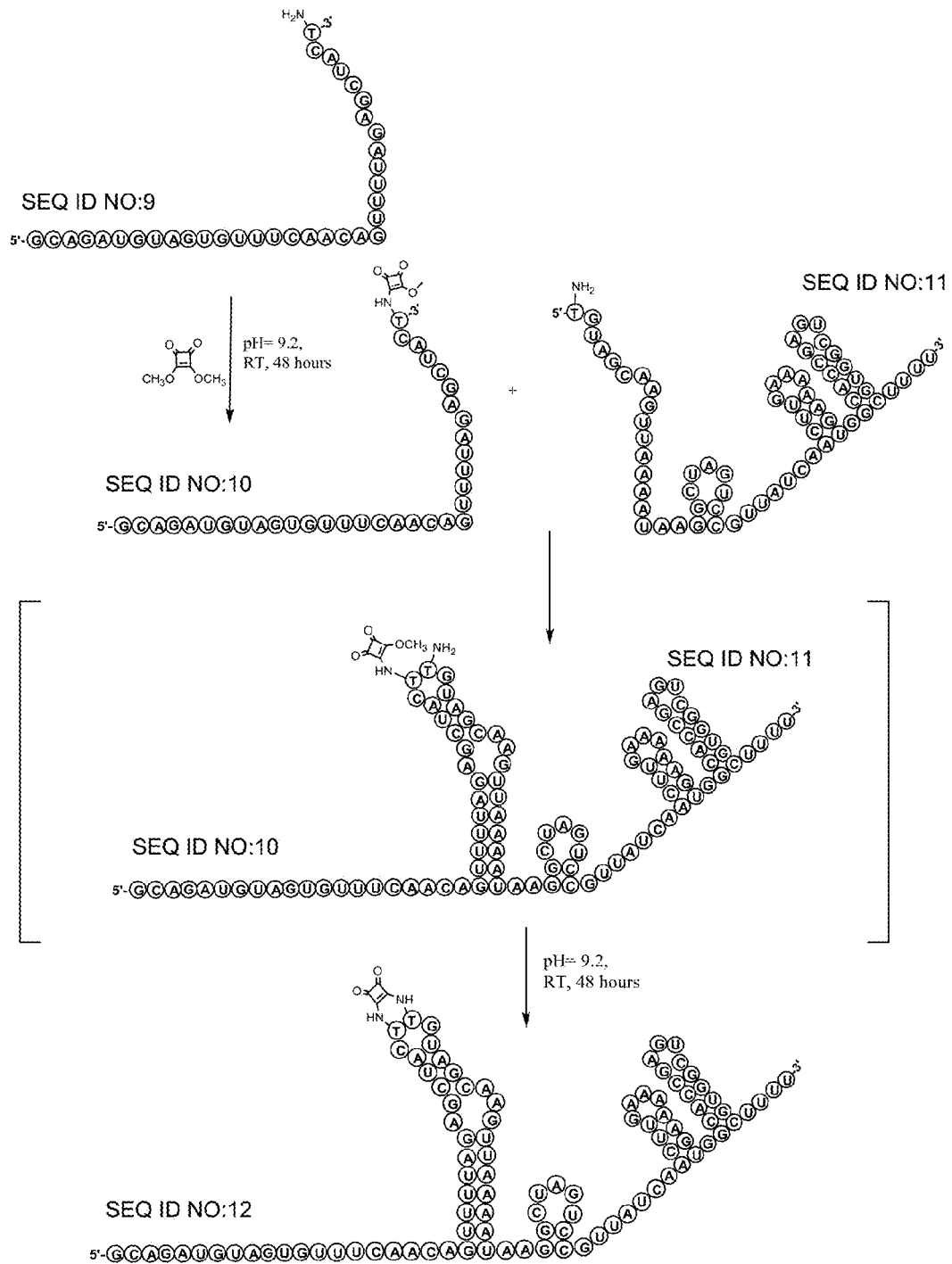
FIG. 11 shows a scheme for the squarate-based coupling of two oligonucleotides via internal splints, e.g., complementary sequences that form stem-loop structures.

The first example of this technique, shown in FIG. 11, uses the tetra loop structure formed by the RNA duplex formation of the two strands to effect squarate coupling.

The 5'-HO-RNA32 mer-dT-NH$_2$-3' strand was converted to the mono squarate by treatment of a 50 mM solution of sodium Borate with excess dimethoxysquarate dissolved in DMSO. After approximately 20 minutes the excess squarate reagent, DMSO and Borate buffer was removed by washing with water in Amicon 3K molecular weight cutoff spin filters until the washings (permeates) showed no UV absorbance (measured over a range of $A_{230\ nm-360\ nm}$). Analysis of the retentate by LCMS showed that the 5'-HO-RNA32 mer-dT-NH-SQ-3' had been formed in >95% yield.

An aqueous solution the 5'HO-RNA32 mer-SQ-NH-dT-3' was mixed with an approximately equal molar amount of 5'-NH$_2$-dT-RNA64 mer-OH-3'. This solution was made 50 mM sodium borate (pH=9.2) and let stand at 22° C. for 48 hours. LCMS analysis showed that the 5'HO-RNA32 mer-SQ-NH-dT-RNA64 mer-OH-3' had been formed.

Figure 12:
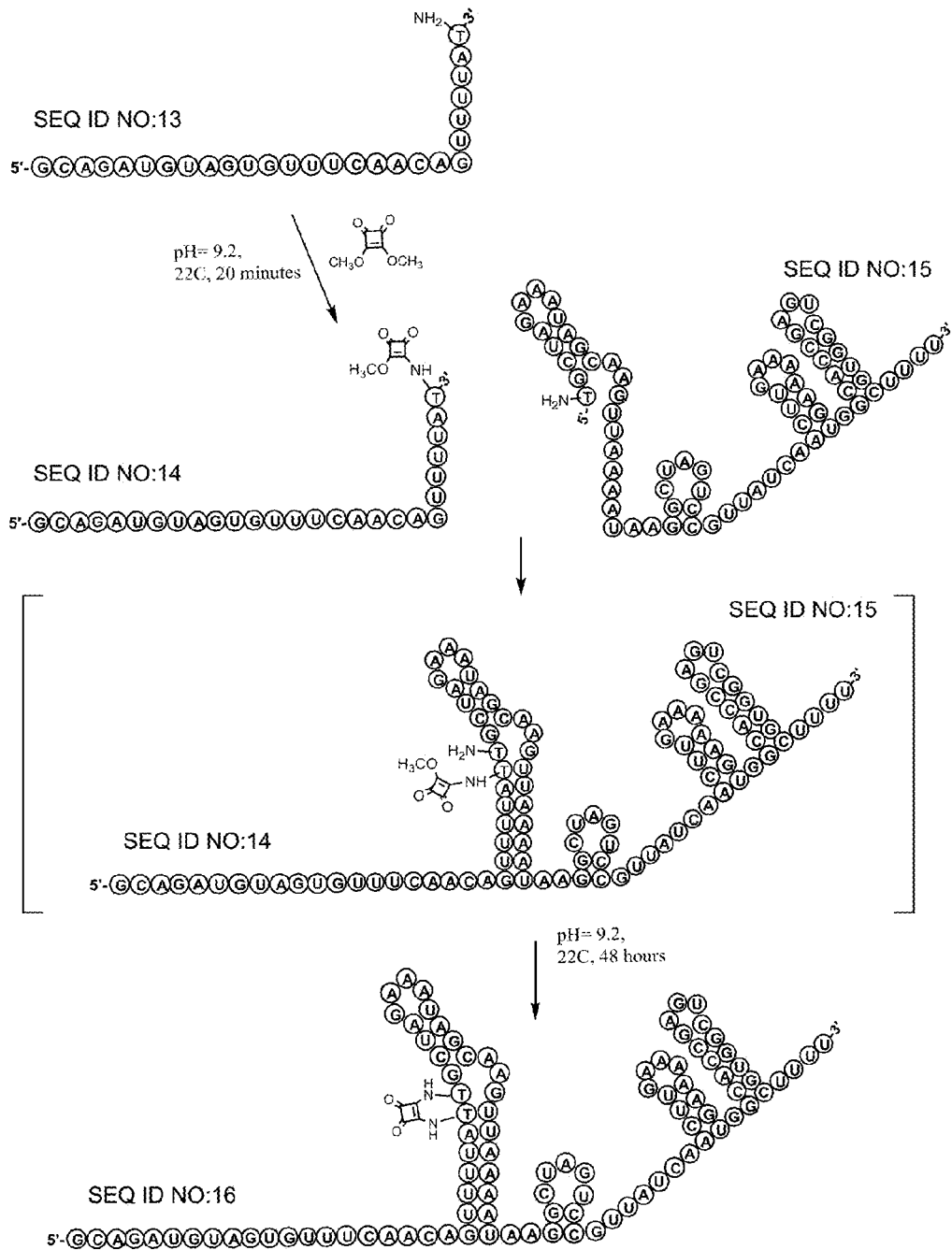
FIG. 12 shows a scheme for the squarate-based coupling of two oligonucleotides via internal splints, e.g., complementary sequences of the two oligonucleotides.

The second example of this technique, shown in FIG. 12, uses a bulge structure formed by the RNA duplex formation of the two strands to affect squarate coupling.

The 5'-HO-RNA25 mer-dT-NH$_2$-3' strand was converted to the mono squarate by treatment of a 50 mM solution of sodium Borate with excess dimethoxysquarate dissolved in DMSO. After approximately 20 minutes the excess squarate reagent, DMSO and Borate buffer was removed by washing with water in Amicon 3K molecular weight cutoff spin filters until the washings (permeates) showed no UV absorbance (measured over a range of $A_{230\ nm-360\ nm}$. Analysis of the retentate by LCMS showed that the 3'-SQ-NH-dT-RNA25 mer-3'OH had been formed in >95% yield.

An aqueous solution the 5'HO-RNA25 mer-SQ-NH-dT-3' was mixed with an approximately equal molar amount of 5'-NH$_2$-dT-RNA71 mer-OH-3'. This solution was made 50 mM sodium borate (pH=9.2) and let stand at 22° C. for 48 hours. LCMS analysis showed that the 5'HO-RNA25 mer-dT-NH-SQ-NH-dT-RNA71 mer-OH-3' had been formed.

Figure 13:
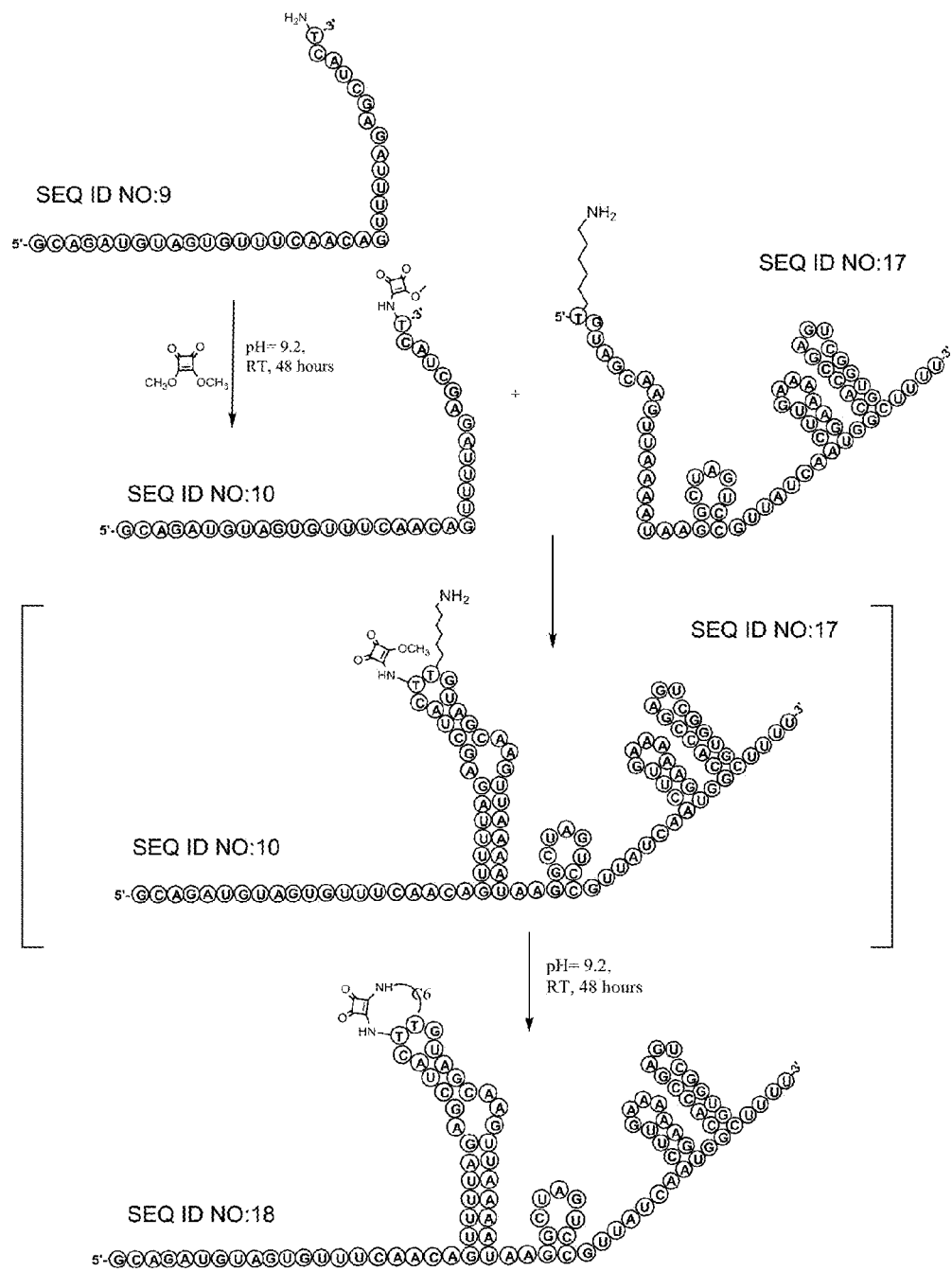
FIG. 13 shows a scheme for the squarate-based coupling of two oligonucleotides via internal splints, e.g., complementary sequences of the two oligonucleotides, where one oligonucleotide has a 5'-amino linker, e.g., a C6-$NH_2$ linker.

The third example of this technique, shown in FIG. 13, uses the tetra loop structure formed by the RNA duplex formation of the two strands to affect squarate coupling. In this instance a 5'amino linker-dT is the 5' coupling end in place of the 5'-NH2-dT species. This example shows the viability of using linker coupling between strands using squarate chemistry.

The 5'-HO-RNA32 mer-dT- $NH_2$-3' strand was converted to the mono squarate by treatment of a 50 mM solution of sodium Borate with excess dimethoxysquarate dissolved in DMSO. After approximately 20 minutes the excess squarate reagent, DMSO and Borate buffer was removed by washing with water in Amicon 3K molecular weight cutoff spin filters until the washings (permeates) showed no UV absorbance (measured over a range of $A_{230\ nm\text{-}360\ nm}$. Analysis of the retentate by LCMS showed that the 5'-HO-RNA32 mer-dT-NH-SQ-3'had been formed in >95% yield.

An aqueous solution the 5'HO-RNA32 mer-dT-NH-SQ-3' was mixed with an approximately equal molar amount of 5'-$NH_2$-C6-dT-RNA64 mer-OH-3'. This solution was made 50 mM sodium borate (pH=9.2) and let stand at 22° C. for 48 hours. LCMS analysis showed that the 5'HO-RNA32 mer dT-NH-SQ-NH-C6-dT-RNA64 mer-OH-3' had been formed.

Example 9

Amplification of a Squarate Ligated DNA Strand

The 140 mer DNA with three squaramide linkages described in Example 3 was successfully used in a PCR experiment. The 140 mer ssDNA product was PCR amplified using Herculase II DNA polymerase (Agilent) or Phusion DNA polymerase (New England Biolabs) using standard PCR reaction conditions. Amplification of the 140 mer tri-squaramide was slightly less efficient compared to the 140 mer DNA all phosphodiester control sequence. The resulting amplicons were directly cloned using the Strata-Clone Blunt PCR cloning kit (Agilent), transformed into supplied competent cells and plated on agar plates, all steps performed following the kit protocol. Colonies were picked into 5 ul of water and sent for rolling circle amplification and Sanger sequencing, forward primer only. Alignments were done between the sequencing reads and the expected 140 base template using a Blast alignment tool. After PCR amplification with Herculase II (Agilent) polymerase, 8% of the TT squaramide linkages had a single T base deletion compared to 22% after amplification with Phusion (NEB) polymerase. These results are summarized in Table 1.

TABLE 1

Sanger sequencing results of 140mer with three squaramide linkages after PCR amplification with two different polymerases.

| Polymerase | # clones Sequenced | Total # of TT sites | # of TT sites with an error* | % of TT sites with error* |
|---|---|---|---|---|
| HerculaseII | 13 | 39 | 3 | 8% |
| Phusion | 12 | 36 | 8 | 22% |

*The error being a single base

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

What is claimed is:

1. A method of conjugating oligonucleotides, comprising:
   activating a terminal of first oligonucleotide using a squarate reagent to produce an activated first oligonucleotide; and
   binding the first oligonucleotide and a second oligonucleotide to a splint oligonucleotide;
   to conjugate the activated first oligonucleotide with a terminal of the second oligonucleotide via a squaramide linkage to produce a squaramide-linked oligonucleotide.

2. The method according to claim 1, wherein:
   the activated first oligonucleotide comprises a terminal squarate monoamide group; and
   the terminal of the second oligonucleotide comprises a terminal amino group.

3. The method according to claim 2, further comprising contacting the second oligonucleotide with a deprotection agent to produce the terminal amino group.

4. The method according to claim 1, wherein the activating step is performed prior to the binding step.

5. The method according to claim 1, wherein the binding step is performed prior to the activating step.

6. The method according to claim 1, wherein the squaramide-linked oligonucleotide is described by Formula (III):

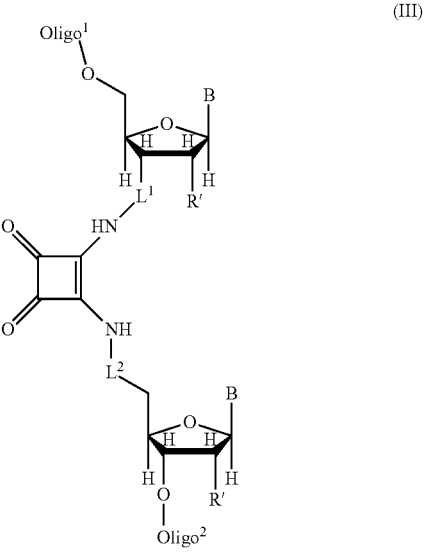

(III)

wherein:
   Oligo[1] is the first oligonucleotide;
   Oligo[2] is the second oligonucleotide;
   each B is independently a nucleobase;

each R' is independently, H, OH, F, or OR, where R is an alkyl, a substituted alkyl or a hydroxyl protecting group; and $L^1$ and $L^2$ are optional linkers.

7. The method according to claim 6, wherein $L^1$ and $L^2$ are each a covalent bond.

8. The method according to claim 1, wherein the splint oligonucleotide is bound to a support.

9. The method according to claim 1, further comprising:
dissociating the squaramide-linked oligonucleotide from the splint oligonucleotide; and binding the squaramide-linked oligonucleotide to a second splint oligonucleotide that includes a region complementaly to a third, oligonucleotide; and
activating a terminal of the squaramide-linked oligonucleotide using a squarate reagent.

10. The method according to claim 1, further comprising:
activating either the second terminal of the first oligonucleotide or a terminal of a third oligonucleotide with a squarate reagent; and
binding the first oligonucleotide and the third oligonucleotide to a second splint oligonucleotide;
to conjugate the first and third oligonucleotides via, a squaramide linkage to produce a squaramide-linked oligonucleotide that comprises two or more squaramide linkages.

11. The method according to claim 10, wherein the first oligomicleotide is bound to the second and third oligonucleotides simultaneously.

12. The method according to claim 10, wherein the first oligonucleotide is bound to the second and third oligonucleotides sequentially.

13. The method according to claim 1, further comprising amplifying the squaramide-linked oligonucleotide using a DNA polymerase.

14. A composition, comprising:
a oligonucleotide sequence comprising 40 or more nucleosides;
a squaramide internucleoside linkage, and
a polymerase.

15. The composition according to claim 14, wherein the oligonucleotide has a sequence comprising 1000 or more nucleosides.

16. The composition according to claim 14, wherein the oligonucleotide has 2 or more squaramide internucleoside linkages.

17. The composition according to claim 14, wherein the oligonucleotide is bound to an array.

18. The composition according to claim 14, wherein the oligonucleotide is cyclic.

19. A composition, comprising:
a first oligonucleotide comprising 300 or more nucleosides and at least one squaramide internucleoside linkage; and
a second oligonucleotide that comprises a sequence complementary to the first oligonucleotide, wherein the second oligonucleotide is a DNA polymerase amplification product of the first oligonucleotide and does not comprise a squaramide linkage.

* * * * *

UNITED STATES PATENT AND TRADEMARK OFFICE
CERTIFICATE OF CORRECTION

PATENT NO. : 9,890,190 B2
APPLICATION NO. : 15/051511
DATED : February 13, 2018
INVENTOR(S) : Kenneth W. Hill et al.

It is certified that error appears in the above-identified patent and that said Letters Patent is hereby corrected as shown below:

In Column 1, Line 63, delete "FIG. 4" and insert -- FIG. 4, --, therefor.

In Column 3, Line 47, delete "propan -1-yl" and insert -- propan-1-yl --, therefor.

In Column 3, Line 63, delete "$R^{3\circ}$" and insert -- $R^{30}$ --, therefor.

In Column 6, Line 15, delete "$OS(O)R^{60}$," and insert -- -$OS(O)_2R^{60}$, --, therefor.

In Column 6, Line 15, delete "-$P(O)(O^{31})_2$," and insert -- -$P(O)(O^-)_2$, --, therefor.

In Column 6, Line 65, delete "cylcoalkyl," and insert -- cycloalkyl, --, therefor.

In Column 6, Line 66, delete "cylcoalkenyl," and insert -- cycloalkenyl, --, therefor.

In Column 7, Line 11, delete "cylcoalkyl," and insert -- cycloalkyl, --, therefor.

In Column 7, Line 12, delete "cylcoalkenyl," and insert -- cycloalkenyl, --, therefor.

In Column 8, Line 37, delete "queosine," and insert -- queuosine, --, therefor.

In Column 19, Line 44, delete "and or" and insert -- and/or --, therefor.

In Column 21, Line 34, delete "-3'with" and insert -- 3' with --, therefor.

In Column 22, Line 17, delete "5'end" and insert -- 5' end --, therefor.

In Column 22, Line 39, delete "30minutes" and insert -- 30 minutes --, therefor.

In Column 23, Line 9, delete "pH7-9.2" and insert -- pH 7-9.2 --, therefor.

Signed and Sealed this
Eighth Day of May, 2018

Andrei Iancu
*Director of the United States Patent and Trademark Office*

CERTIFICATE OF CORRECTION (continued)
U.S. Pat. No. 9,890,190 B2

In Column 23, Line 11, delete "soluton." and insert -- solution. --, therefor.

In Column 23, Line 41, delete "iss" and insert -- is --, therefor.

In Column 26, Line 10, delete "and or" and insert -- and/or --, therefor.

In Column 26, Line 11, delete "and or" and insert -- and/or --, therefor.

In Column 27, Line 15, delete "-SQ-3'had" and insert -- -SQ-3' had --, therefor.

In Column 37, Line 14, in Claim 9, delete "complementaly" and insert -- complementary --, therefor.

In Column 37, Line 14, in Claim 9, delete "third," and insert -- third --, therefor.

In Column 37, Line 24, in Claim 10, delete "via," and insert -- via --, therefor.

In Column 37, Line 29, in Claim 11, delete "oligomicleotide" and insert -- oligonucleotide --, therefor.